(12) United States Patent
Evans

(10) Patent No.: US 9,051,320 B1
(45) Date of Patent: Jun. 9, 2015

(54) METHODS FOR THE TREATMENT OF METABOLIC DISORDERS BY A SELECTIVE SMALL MOLECULE AUTOTAXIN INHIBITOR

(71) Applicant: PharmAkea, Inc., San Diego, CA (US)

(72) Inventor: Jillian Frances Evans, San Diego, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

(21) Appl. No.: 14/462,459

(22) Filed: Aug. 18, 2014

(51) Int. Cl.
| | | |
|---|---|---|
| A61K 31/405 | (2006.01) | |
| C07D 471/14 | (2006.01) | |
| A61K 31/437 | (2006.01) | |
| C07D 403/04 | (2006.01) | |
| A61K 31/4155 | (2006.01) | |
| C07D 401/14 | (2006.01) | |
| A61K 31/4439 | (2006.01) | |
| C07D 403/06 | (2006.01) | |
| A61K 31/4025 | (2006.01) | |
| A61K 45/06 | (2006.01) | |

(52) U.S. Cl.
CPC ............ *C07D 471/14* (2013.01); *A61K 31/437* (2013.01); *C07D 403/04* (2013.01); *A61K 31/4155* (2013.01); *C07D 401/14* (2013.01); *A61K 31/4439* (2013.01); *C07D 403/06* (2013.01); *A61K 31/4025* (2013.01); *A61K 45/06* (2013.01); *A61K 31/405* (2013.01)

(58) Field of Classification Search
CPC ............................. A61K 31/405; A61K 45/06
See application file for complete search history.

(56) References Cited

U.S. PATENT DOCUMENTS

| | | |
|---|---|---|
| 5,186,522 A | 2/1993 | Spencer |
| 5,210,574 A | 5/1993 | Kita |
| 5,538,444 A | 7/1996 | Strand et al. |
| 5,564,676 A | 10/1996 | Goloff et al. |
| 5,564,949 A | 10/1996 | Wellinsky |
| 5,711,925 A | 1/1998 | Noda et al. |
| 5,761,473 A | 6/1998 | Kahle et al. |
| 7,839,888 B2 | 11/2010 | Jung et al. |
| 7,905,958 B2 | 3/2011 | Sasaki et al. |
| 7,921,385 B2 | 4/2011 | Abrams et al. |
| 8,022,239 B2 | 9/2011 | Parrill-baker et al. |
| 8,268,891 B1 | 9/2012 | Parrill-baker et al. |
| 8,329,907 B2 | 12/2012 | Schultz et al. |
| 8,343,934 B2 | 1/2013 | Parrill-baker et al. |
| 8,378,100 B2 | 2/2013 | Lynch et al. |
| 8,497,371 B2 | 7/2013 | Parrill-baker et al. |
| 8,530,650 B2 | 9/2013 | Schiemann et al. |
| 8,552,001 B2 | 10/2013 | Schiemann et al. |
| 8,557,824 B2 | 10/2013 | Schiemann et al. |
| 8,673,882 B2 | 3/2014 | Gupte et al. |
| 2006/0270634 A1 | 11/2006 | Miller et al. |
| 2010/0016258 A1 | 1/2010 | Lynch et al. |
| 2010/0136650 A1 | 6/2010 | Parrill-Baker et al. |
| 2010/0222341 A1 | 9/2010 | Schiemann et al. |
| 2010/0240676 A1 | 9/2010 | Schiemann et al. |
| 2010/0249132 A1 | 9/2010 | Schultz et al. |
| 2011/0110886 A1 | 5/2011 | Braddock |
| 2011/0160148 A1 | 6/2011 | Parrill-baker et al. |
| 2011/0230471 A1 | 9/2011 | Staehle et al. |
| 2011/0237583 A1 | 9/2011 | Schiemann et al. |
| 2012/0015959 A1 | 1/2012 | Staehle et al. |
| 2012/0015976 A1 | 1/2012 | Schultz et al. |
| 2012/0059016 A1 | 3/2012 | Schiemann et al. |
| 2012/0100592 A1 | 4/2012 | Parrill-baker et al. |
| 2012/0115852 A1 | 5/2012 | Schultz et al. |
| 2012/0190650 A1 | 7/2012 | Gupte et al. |
| 2012/0202827 A1 | 8/2012 | Schiemann et al. |
| 2013/0012505 A1 | 1/2013 | Staehle et al. |
| 2013/0029948 A1 | 1/2013 | Roppe et al. |
| 2013/0150326 A1* | 6/2013 | Roppe et al. ............ 514/64 |
| 2013/0251728 A1 | 9/2013 | Harp et al. |
| 2014/0113953 A1 | 4/2014 | Stoffel et al. |
| 2014/0171361 A1 | 6/2014 | Jonker et al. |
| 2014/0171403 A1 | 6/2014 | Legrand et al. |
| 2014/0171404 A1 | 6/2014 | Furminger et al. |
| 2014/0200231 A1 | 7/2014 | Beauchamp et al. |

FOREIGN PATENT DOCUMENTS

| | | |
|---|---|---|
| WO | WO-2008-157361 | 12/2008 |
| WO | WO-2009-046804 | 4/2009 |
| WO | WO-2009-046841 | 4/2009 |
| WO | WO-2009-046842 | 4/2009 |
| WO | WO-2009-151644 | 12/2009 |
| WO | WO-2010-040080 | 4/2010 |
| WO | WO-2010-060532 | 6/2010 |
| WO | WO-2010-063352 | 6/2010 |
| WO | WO-2010-112116 | 10/2010 |
| WO | WO-2010-112124 | 10/2010 |
| WO | WO-2010-115491 | 10/2010 |
| WO | WO-2010-132479 | 11/2010 |
| WO | WO-2011-002918 | 1/2011 |
| WO | WO-2011-006569 | 1/2011 |
| WO | WO-2011-044978 | 4/2011 |
| WO | WO-2011-053597 | 5/2011 |
| WO | WO-2011-116867 | 9/2011 |
| WO | WO-2012-024620 | 2/2012 |
| WO | WO-2012-100018 | 7/2012 |
| WO | WO-2012-166415 | 12/2012 |
| WO | WO-2013-054185 | 4/2013 |
| WO | WO-2013-061297 | 5/2013 |
| WO | WO-2013-186159 | 12/2013 |
| WO | WO-2014-048865 | 4/2014 |
| WO | WO-2014-097151 | 6/2014 |

OTHER PUBLICATIONS

Federico et al., Mol. Endocr. 26: 786-797, 2012.*
Boucher et al., Diabetologia 48: 569-577, 2005.*
Zou et al., Vasc. Health and Risk Management 9, 429-433, 2013.*
U.S. Appl. No. 61/878,922, filed Sep. 17, 2013, Hutchinson et al.
U.S. Appl. No. 61/878,945, filed Sep. 17, 2013, Hutchinson et al.

(Continued)

*Primary Examiner* — Gyan Chandra
(74) *Attorney, Agent, or Firm* — Wilson Sonsini Goodrich & Rosati

(57) ABSTRACT

Described herein are methods and compositions for treatment or prevention of metabolic disorder(s) in an individual. The methods and compositions disclosed herein include the use of at least one autotaxin inhibitor compound.

19 Claims, 3 Drawing Sheets

(56) References Cited

OTHER PUBLICATIONS

U.S. Appl. No. 61/883,026, filed Sep. 26, 2013, Hutchinson et al.
U.S. Appl. No. 61/907,947, filed Nov. 22, 2013, Hutchinson et al.
U.S. Appl. No. 61/907,965, filed Nov. 22, 2013, Hutchinson et al.
Albers et al. Boronic acid-based inhibitor of autotaxin reveals rapid turnover of LPA in the circulation. Proc. Natl. Acad. Sci. USA 2010 107:7257-7262.
Albers et al. Chemical evolution of autotaxin inhibitors. Chem. Rev. 2012 112:2593-2603.
Albers et al. Discovery and optimization of boronic acid based inhibitors of autotaxin. J. Med. Chem. 2010 53:4958-4967.
Albers et al. Structure-based design of novel boronic acid-based inhibitors of autotaxin. J. Med. Chem. 2011 54:4619-4626.
Baker et al. Carba analogs of cyclic phosphatidic acid are selective inhibitors of autotaxin and cancer cell invasion and metastasis. J. Biol. Chem. 2006 281:22786-22793.
Barbayianni et al. Autotaxin inhibitors: a patent review. Expert Opin Ther Pat. 2013 23(9):1123-1132.
Berge et al. Pharmaceutical Salts. J. Pharm. Sci. 1977 66:1-19.
Bosarge et al. Stress-induced Hyperglycemia. Is It Harmful Following Trama? Advances in Surgery. 2013. 47:287-297.
Bundgaard. Advanced Drug Delivery Review 1992 8:1-38.
Bundgaard. Design and Application of Prodrugs. A Textbook of Drug Design and Development 1991 Chapter 5, p. 113-191.
Bundgard. Design of Prodrugs. Elseview, 1985.
Cui et al. alpha- and beta-substituted phosphonate analogs of LPA as autotaxin inhibitors. Bioorg. Med. Chem. 2008 16:2212-2225.
Cui et al. Synthesis and biological evaluation of phosphonate derivatives as autotaxin (ATX) inhibitors. Bioorg. Med. Chem. Lett. 2007 17:1634-1640.
Diagnosis and Classification of Diabetes Mellitus. Diabetes Care. 2014. 37(Supp. 1):S81.
Durgam et al. Synthesis, structure-activity relationships, and biological evaluation of fatty alcohol phosphates as lysophosphatidic acid receptor ligands, activators of PPARgamma, and inhibitors of autotaxin. J. Med. Chem. 2005 48:4919-4930.
Durgam et. al. Synthesis and pharmacological evaluation of second-generation phosphatidic acid derivatives as lysophosphatidic acid receptor ligands. Bioorg. Med. Chem. Lett. 2006 16:633-640.
Dusaulcy et al. Adipose-specific disruptions of autotaxin enhances nutritional fattening and reduces plasma lysophosphatidic acid. J of Lipid Research. 2011. 52:1247-1255.
East et al. Synthesis and structure-activity relationships of tyrosine-based inhibitors of autotaxin (ATX). Bioorg. Med. Chem. Lett. 2010 20:7132-7136.
Federico et al. Therapeutic potential of autotaxin/lysophospholipase d inhibitors. Curr Drug Targets 2008 9(8):698-708.
Ferry et al. 532826, A Nanomolar Inhibitor of Autotaxin: Discovery, Synthesis and Applications as a Pharmacological Tool. J. Pharmacol. Exp. Ther. 2008 327:809-819.
Gajewak et al. Synthesis, pharmacology, and cell biology of sn-2-aminooxy analogues of lysophosphatidic acid. Org. Lett. 2008 10:1111-1114.
Gendaszewska-Darmach et al. The chemical synthesis of metabolically stabilized 2-OMe-LPA analogues and preliminary studies of their inhibitory activity toward autotaxin. Bioorg. Med. Chem. Lett. 2012 22:2698-2700.
Gierse et al. A novel autotaxin inhibitor reduces lysophosphatidic acid levels in plasma and the site of inflammation. J. Pharmacol. Exp. 2010 334 :310-317.
Gududuru et al. Identification of Darmstoff analogs as selective agonists and antagonists of lysophosphatidic acid receptors. Bioorg. Med. Chem. Lett. 2006 16:451-456.
Gupte et al. Benzyl and naphthalene methylphosphonic acid inhibitors of autotaxin with anti-invasive and anti-metastatic activity. ChemMedChem 2011 6:922-935.
Gupte et al. Synthesis and pharmacological evaluation of the stereoisomers of 3-carba cyclic-phosphatidic acid. Bioorg. Med. Chem. Lett. 2010 20:7525-7528.
Hoeglund et al. Optimization of a pipemidic acid autotaxin inhibitor. J. Med. Chem. 2010 53:1056-1066.
Hoeglund et al. Characterization of non-lipid autotaxin inhibitors. Bioorg. Med. Chem. 2010 18:769-776.
Jiang et al. Alpha-substituted phosphonate analogues of lysophosphatidic acid (LPA) selectively inhibit production and action of LPA. ChemMedChem 2007 2:679-690.
Jiang et al. Aromatic phosphonates inhibit the lysophospholipase D activity of autotaxin. Bioorg. Med. Chem. Lett. 2011 21:5098-5101.
Kano et al. LPA and its analogs-attractive tools for elucidation of LPA biology and drug development. Curr. Med. Chem. 2008 15:2122-2131.
Moulharat et al. Molecular pharmacology of adipocyte-secreted autotaxin. Chem.-Biol. Interact. 2008 172:115-124.
Nishimura et al. ENPP2 contributes to adipose tissue expansion in diet-induced obesity. Diabetes. 2014. Epub ahead of print. Published online Jun. 26, 2014. doi: 10.2337/db13-1694. 45 pages.
North et al. Pharmacophore development and application toward the identification of novel, small-molecule autotaxin inhibitors. J. Med. Chem. 2010 53:3095-3105.
Parrill et al. Autotaxin Inhibitors: A Persepctive on Initial Medicinal Chemisty Efforts. Expert Opin Ther Pat 2010 20(12):1619-1625.
Parrill et al. Virtual screening approaches for the identification of non-lipid autotaxin inhibitors. Bioorg. Med. Chem. 2008 16:1784-1795.
Rancoule et al. Depot-specific regulation of autotaxin with obesity in human adipose tissue. J Physiol Biochem. 2012. 68:635-644.
Rancoule et al. Lysophosphatidic acid impairs glucose homeostasis and inhibits insulin secretion in high-fat diet obese mice. Diabetolgia. 2013. 9 pgs.
Rehman et al. Drug-Induced Glucose Alterations Part 2: Drug-Induced Hyperglycemia. Diabetes Spectrum. 2011. 24(4):234-238.
Saunders et al. Identification of small-molecule inhibitors of autotaxin that inhibit melanoma cell migration and invasion. Mol. Cancer Ther. 2008 7:3352-3362.
Skyler. Effects of Glycemic Control on Diabetes Complications and on the Prevention of Diabetes. Clinical Diabetes. 2004. 22(4):162-166.
Standards of Medical care in Diabetes—2014. Diabetes Care. 2014. 37(Supp. 1):S14.
Tanaka et al. Efficient synthesis of 3-O-thia-cPA and preliminary analysis of its biological activity toward autotaxin. Bioorg. Med. Chem. Lett. 2011 21:4180-4182.
Turner et al. Glycemic Control With Diet, Sulfonylurea, Metformin, or Insulin in Patients With Type 2 Diabetes Mellitus: Progressive Requirement for Multiple Therapies (UUKPDS 49). JAMA, 281(21):2005-2012. 1999.
van Meeteren et al. Anticancer activity of FTY720: phosphorylated FTY720 inhibits autotaxin, a metastasis-enhancing and angiogenic lysophospholipase D. Cancer Lett. 2008 266:203-208.
van Meeteren et al. Inhibition of autotaxin by lysophosphatidic acid and sphingosine 1-phosphate. J. Biol. Chem. 2005 280:21155-21161.
Zhang et al. Dual activity lysophosphatidic acid receptor pan-antagonist/autotaxin inhibitor reduces breast cancer cell migration in vitro and causes tumor regression in vivo. Cancer Res 2009 69:5441-5449.
Aljammal et al. Serum Autotaxin Correlates with Insulin Resistance and Features of the Metabolic Syndrome in Humans. Poster and Abstract. Jun. 2014.

\* cited by examiner

US 9,051,320 B1

METHODS FOR THE TREATMENT OF METABOLIC DISORDERS BY A SELECTIVE SMALL MOLECULE AUTOTAXIN INHIBITOR

BACKGROUND OF THE INVENTION

Autotaxin (ATX), also known as ectonucleotide pyrophosphatase/phosphodiesterase family member 2 or ENNP2, is an adipocyte secreted lysophospholipase D that catalyzes the formation of the lipid mediator, lysophospatidic acid (LPA). ATX is secreted by adipose tissue and its expression is enhanced in individuals with metabolic disorders.

SUMMARY OF THE INVENTION

The autotaxin-lysophosphatidic acid signaling pathway has been implicated in a variety of signaling pathways involved in cell migration, proliferation, and survival. Due to its role in these pathways, autotaxin has been explored in the last decade as a drug discovery target for the treatment of chronic inflammation, neuropathic pain, fibrotic disease, and various cancers. Intensive efforts have focused on identifying autotaxin inhibitors in the treatment of these disorders.

Provided herein are methods for treating metabolic disorders, and conditions associated with metabolic disorders, comprising administering an autotaxin inhibitor to an individual in need thereof.

Provided herein are methods for reducing blood glucose levels of a subject comprising administering to the subject an autotaxin inhibitor; and thereby decreasing the blood glucose levels of the subject.

In some embodiments, the subject has an elevated blood glucose level. In certain embodiments, the methods comprise measuring the blood glucose level of the subject. In certain embodiments, the methods comprise selecting a subject having an elevated blood glucose level. In certain embodiments, the blood glucose level is a fasted blood glucose level. In certain embodiments, the blood glucose level is a post-prandial blood glucose level. In certain embodiments, the blood glucose level is a whole blood glucose level. In certain embodiments, the blood glucose level is a plasma blood glucose level.

In some embodiments, the blood glucose level is reduced to below 200 mg/dL. In certain embodiments, the blood glucose level is reduced to below 175 mg/dL. In certain embodiments, the blood glucose level is reduced to below 150 mg/dL. In certain embodiments, the blood glucose level is reduced to below 125 mg/dL. In certain embodiments, the blood glucose level is reduced to below 120 mg/dL. In certain embodiments, the blood glucose level is reduced to below 115 mg/dL. In certain embodiments, the blood glucose level is reduced to below 110 mg/dL. In certain embodiments, the blood glucose level is reduced to below 105 mg/dL. In certain embodiments, the blood glucose level is reduced to below 100 mg/dL.

Provided herein are methods for preventing or delaying the onset of an elevated blood glucose level in a subject at risk for developing an elevated glucose level comprising administering to the subject an autotaxin inhibitor.

Provided herein are methods for reducing plasma lysophosphatidic acid levels of a subject comprising administering to the subject an autotaxin inhibitor; and thereby decreasing plasma lysophosphatidic acid levels of a subject. In some embodiments, the subject has an elevated blood glucose level. In some embodiments the subject is insulin resistant.

Provided herein are methods for improving insulin sensitivity in a subject comprising administering to the subject an autotaxin inhibitor; and thereby improving insulin resistance in the subject.

Provided herein are methods for preventing or delaying the onset of insulin resistance in a subject at risk for developing insulin resistance comprising administering to the subject an autotaxin inhibitor; and thereby preventing or delaying the onset of insulin resistance in the subject. In certain embodiments, the methods comprise selecting a subject at risk for developing insulin resistance.

Provided herein are methods for increasing insulin secretion in a subject comprising administering to the subject an autotaxin inhibitor; and thereby increasing insulin secretion in the subject. In some embodiments, the subject has an elevated blood glucose level.

Provided herein are methods for improving glucose tolerance in a subject comprising administering to the subject an autotaxin inhibitor; and thereby improving glucose tolerance.

Provided herein are methods for decreasing adipose tissue expansion in a subject comprising administering to the subject an autotaxin inhibitor; and thereby decreasing adipose tissue expansion in the subject. In some embodiments, the subject has an elevated blood glucose level. In some embodiments, the subject is insulin resistant.

In any of the methods, the subject optionally has a metabolic disorder.

Provided herein are methods for treating a metabolic disorder with an autotaxin inhibitor. In some embodiments, the metabolic disorder is treated by reducing blood glucose levels. In some embodiments, the metabolic disorder is treated by reducing plasma lysophosphatidic acid levels. In some embodiments, the metabolic disorder is treated by improving insulin sensitivity. In some embodiments, the metabolic disorder is treated by increasing insulin secretion. In some embodiments, the metabolic disorder is treated by improving glucose tolerance. In some embodiments, the metabolic disorder is treated by decreasing adipose tissue expansion. In some embodiments, the metabolic disorder does not induce hypoglycemia.

Provided herein are methods for preventing or delaying the onset of at least one metabolic disorder in a subject at risk for developing a metabolic disorder, comprising administering to the subject an autotaxin inhibitor.

In some embodiments, the metabolic disorder is selected from the group consisting of: metabolic syndrome, elevated blood glucose levels, insulin resistance, glucose intolerance, type 2 diabetes, type 1 diabetes, pre-diabetes, non-alcoholic fatty liver disease (NAFLD), nonalcoholic steatohepatitis (NASH) and obesity.

In some embodiments, the autotaxin inhibitor is administered with at least one additional therapy. In some embodiments, the at least one additional therapy is a glucose-lowering agent. In some embodiments, the glucose-lowering agent is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the at least one additional therapy is metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, the at least one additional therapy is a lipidlowering agent. In some embodiments, the at least one additional therapy is a therapy used to treat cardiovascular disease. In some embodiments, the therapy used to treat cardiovascular disease is an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, and a fibrate, and any combination thereof. In certain embodiments, the at least one additional therapy is administered at the same time as the autotaxin inhibitor. In certain embodiments, the at least one additional therapy is administered less frequently than the autotaxin inhibitor. In certain embodiments, the at least one additional therapy is administered more frequently than the autotaxin inhibitor. In certain embodiments, the at least one additional therapy is administered prior to administration of the autotaxin inhibitor. In certain embodiments, the at least one additional therapy is administered after administration of the autotaxin inhibitor.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
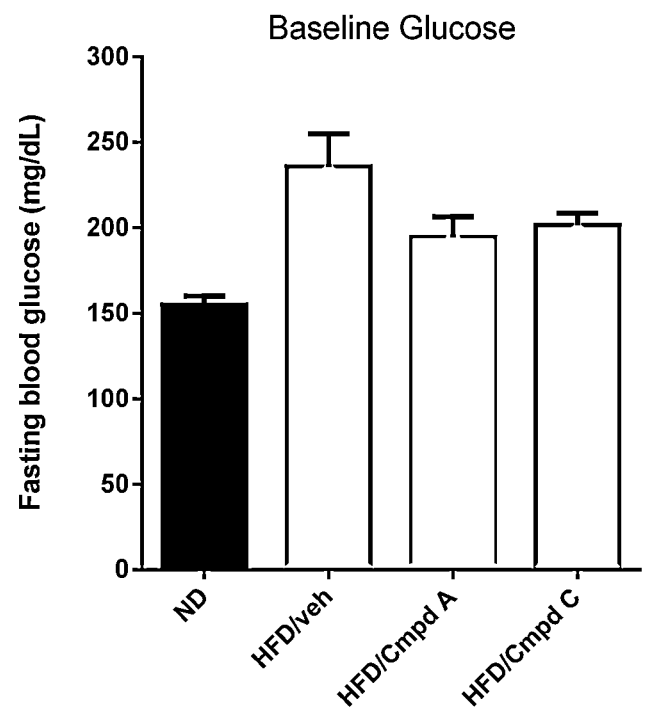
FIG. 1 illustrates the effects of autotaxin inhibitors (Compound A and Compound C) on fasting blood glucose levels in mice fed a high fat diet (HFD). Baseline fasting blood glucose (top graph) from normal diet (ND) mice and high fat diet mice dosed orally with vehicle (veh), Compound A (30 mg/kg) or Compound C (15 mg/kg) twice daily for two days prior to sampling and once on the day of sampling. Total blood glucose AUC (bottom graph) from these same mice after an i.p. challenge with 1 g/kg glucose.
Figure 1:
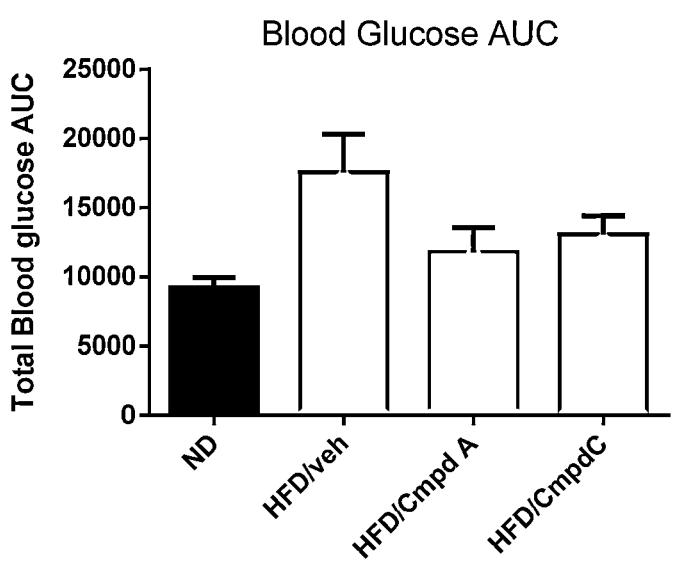

Provided herein are methods for treating metabolic disorders, and conditions associated with metabolic disorders, comprising administering an autotaxin inhibitor. As used herein, a "metabolic disorder" refers to any pathological condition resulting from an alteration in a subject's metabolism. Such disorders include those resulting from an alteration in glucose homeostasis and/or insulin dysfunction. Metabolic disorders, include but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis, and obesity.

Metabolic disorders are inter-related and can result in disorders across various systems. Addressing the core metabolic disorder can reduce the severity of related conditions in a patient, including, e.g.: cardiovascular disorders (including, e.g., ischemic heart disease, angina and myocardial infarction, congestive heart failure, high blood pressure, abnormal cholesterol levels, deep vein thrombosis, and pulmonary embolism), neurological disorders (including, e.g., stroke, meralgia paresthetica, migraines, idiopathic, and intracranial hypertension, depression and social stigmatism), rheumatological and orthopedic disorders (including, e.g., gout, poor mobility, osteoarthritis, and lower back pain), dermatological disorders (including, e.g., stretch marks, acanthosis nigricans, lymphedema, cellulitis), gastrointestinal disorders (including, e.g., gastroesophageal reflux disease (GERD) and cholelithiasis (gallstones)), respiratory disorders (including, e.g., obstructive sleep apnea, obesity hypoventilation syndrome, asthma, and increased complications during general anaesthesia), urology and nephrology disorders (including, e.g., erectile dysfunction, urinary incontinence, chronic renal failure, and hypogonadism).

Provided herein are methods for treating metabolic disorders. In some embodiments, administering an autotaxin inhibitor to an individual with a metabolic disorder has a variety of desirable outcomes which include, but are not limited to, reducing blood glucose levels, decreasing plasma lysophosphatidic acid levels, improving insulin sensitivity, increasing insulin secretion, improving glucose tolerance, and decreasing adipose tissue expansion. Any of these outcomes can treat, delay or prevent the onset of a metabolic disorder, wherein such metabolic disorders include, but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis, and obesity.

As disclosed herein, the administration of an autotaxin inhibitor reduced fasting blood glucose levels in a mouse fed a high fat diet. A mouse fed a high fat diet, as illustrated herein, has higher fasting blood glucose levels than a mouse fed a normal diet. The administration of an autotaxin inhibitor to a mouse fed a high fat diet reduced fasting blood glucose levels thereby allowing fasting blood glucose levels to approach those levels observed in a mouse fed a normal diet.

In some embodiments, methods disclosed herein comprise administering an autotaxin inhibitor to a subject with elevated blood glucose levels. In some embodiments, the autotaxin inhibitor is used to treat an underlying metabolic disorder. In some embodiments, the metabolic disorder is treated by reducing blood glucose levels. In some embodiments, the subject is overweight or obese. In some embodiments, the subject has type 2 diabetes. In some embodiments, the subject has non-alcoholic fatty liver disease and/or nonalcoholic steatohepatitis. In some embodiments, the subject does not have a metabolic disorder. In some embodiments, the autotaxin inhibitor delays or prevents the onset of the metabolic disorder by reducing elevated blood glucose levels.

Also described herein are methods for reducing plasma lysophosphatidic acid levels in an individual. In some embodiments, the plasma lysophosphatidic acid levels in the individual are elevated relative to a control. In some embodiments, the control is a person without a metabolic disorder. In some embodiments, the elevated plasma lysophosphatidic acid levels in the individual contribute to or increase the risk for developing a metabolic disorder.

Autotaxin (ATX, NPP2, or E-NPP2), an approximately 120 kDa glycoprotein, is a secreted nucleotide pyrophosphatase/phosphodiesterase with lysophospholipase D activity that converts extracellular lysophosphatidylcholine and other lysophospholipids to lysophosphatidic acid. Autotaxin is considered to be responsible for the majority of circulating lysophosphatidic acid (LPA) production. Lysophosphatidic acid acts through sets of specific G protein-coupled receptors (GPCRs), such as LPA1, LPA2, LPA3, LPA4, LPA5, LPA6, LPA7, LPA8, in an autocrine and paracrine fashion to produce a variety of biological responses.

Autotaxin is abundantly secreted by adipose tissue which leads to the local and systemic production of lysophosphatidic acid. In metabolic disease, lysophosphatidic acid has a negative effect on glucose homeostasis. In a comparison of mice fed a high fat diet with mice fed a normal diet, the mice fed a high fat diet have higher levels of lysophosphatidic acid. Studies have shown that the administration of the lysophosphatidic acid inhibitor, Ki16425, reverses the negative impact of lysophosphatidic acid has on glucose homeostasis. Chronic treatment with Ki16425 to mice fed a high fat diet improves insulin sensitivity, increases liver glycogen storage, and increases the capacity of a muscle to oxidize glucose, and improves fasting insulin levels.

Accordingly, the methods disclosed herein comprise administering an autotaxin inhibitor to a subject with elevated plasma lysophosphatidic acid levels relative to a control. In some embodiments the control is a person without a metabolic disorder. In some embodiments, the autotaxin inhibitor is used to treat an underlying metabolic disorder. In some embodiments, the metabolic disorder is treated by reducing plasma lysophosphatidic acid levels. In some embodiments, the subject has decreased insulin sensitivity. In some embodiments, insulin sensitivity in the subject is improved by decreasing plasma lysophosphatidic acid levels. In some embodiments, the subject has elevated blood glucose levels. In some embodiments, the elevated blood glucose levels are reduced by reducing lysophosphatidic acid levels. In some embodiments, the subject does not have a metabolic disorder. In some embodiments, the autotaxin inhibitor delays or prevents the onset of the metabolic disorder by reducing plasma lysophosphatidic acid levels.

As described herein are methods for improving insulin sensitivity. Autotaxin is abundantly produced by adipocytes, and expression of autotaxin increases with obesity in association with insulin resistance. In studies examining massively obese individuals, those individuals which show diabetic or pre-diabetic symptoms show increased expression of autotaxin, whereas those massively obese patients that did not show diabetic or pre-diabetic symptoms have lower levels of autotaxin.

In certain embodiments, a subject having elevated blood glucose levels is insulin resistant. One of the main functions of insulin is to lower blood glucose levels. A subject whose cells are sensitive to the effects of insulin needs only a relatively small amount of insulin to keep blood glucose levels in the normal range. A subject who is insulin resistant requires more insulin to get the same blood glucose-lowering effects. Insulin resistance may cause hyperinsulinemia. Hyperinsulinemia may be associated with high blood pressure, heart disease and heart failure, obesity (particularly abdominal obesity), osteoporosis, and certain types of cancer, such as colon, breast, and prostate cancer.

Insulin resistance may be detected using a procedure known as the hyperinsulinemic euglycemic clamp, which measures the amount of glucose necessary to compensate for an increased insulin level without causing hypoglycemia. During the procedure, insulin is infused at 10-120 mU per m2 per minute. In order to compensate for the insulin infusion, a 20% solution of glucose is infused to maintain blood sugar levels between 5 and 5.5 mmol/L. The rate of glucose infusion is determined by checking the blood sugar levels every 5 to 10 minutes. Low-dose insulin infusions are more useful for assessing the response of the liver, whereas high-dose insulin infusions are useful for assessing peripheral (i.e., muscle and fat) insulin action. The rate of glucose infusion during the last 30 minutes of the test determines insulin sensitivity. If high levels (7.5 mg/min or higher) are required, the subject is insulin-sensitive. Very low levels (4.0 mg/min or lower) indicate that the subject is resistant to insulin action. Levels between 4.0 and 7.5 mg/min are not definitive and suggest impaired glucose tolerance. Impaired glucose tolerance may be an early sign of insulin resistance. Glucose tracers, such as 3-3H glucose, 6,62H-glucose, or 1-13C glucose, may be used in the procedure. Other radioactive forms of glucose may be employed in a research setting. Prior to beginning the hyperinsulinemic period, a 3 hour tracer infusion enables the determination of the basal rate of glucose production. During the clamp procedure, the plasma tracer concentrations enable the calculation of whole-body insulin-stimulated glucose metabolism, as well as the production of glucose by the body (i.e., endogenous glucose production).

Accordingly, the methods disclosed herein comprise administering an autotaxin inhibitor to a subject with insulin resistance. In some embodiments, the autotaxin inhibitor improves insulin sensitivity. In some embodiments, the autotaxin inhibitor treats a metabolic disorder. In some embodiments, the autotaxin inhibitor treats a metabolic disorder by improving insulin sensitivity. In some embodiments, the subject does not have a metabolic disorder. In some embodiments, the autotaxin inhibitor delays or prevents the onset of the metabolic disorder by improving insulin sensitivity.

As described herein, are methods for improving insulin secretion. In mice fed a normal diet and in mice fed a high fat diet, injection of exogenous lysophosphatidic acid impairs glucose-induced insulin secretion. In some embodiments, the autotaxin inhibitor improves insulin secretion by decreasing the level of lysophosphatidic acid. In some embodiments, a metabolic disorder is treated by increasing insulin secretion. In some embodiments, the subject does not have a metabolic disorder. In some embodiments, the autotaxin inhibitor delays or prevents the onset of the metabolic disorder by increasing insulin secretion.

As described herein, are methods for improving glucose tolerance. In mice fed a normal diet and in mice fed a high fat diet, injection of exogenous lysophosphatidic acid impairs glucose tolerance. Injection of the inhibitor of lysophosphatidic acid, Ki16425, does not significantly improve glucose tolerance in mice fed a normal diet, but does significantly improve glucose tolerance in mice fed a high fat diet. Further, transgenic mouse studies in which autotaxin is selectively deleted from adipocyte tissue improves glucose intolerance and insulin resistance induced by a high fat diet.

In some embodiments, described herein is a method of improving glucose tolerance in an individual comprising administering an autotaxin inhibitor to the subject with impaired glucose tolerance. In some embodiments, the autotaxin inhibitor improves glucose tolerance in the individual by decreasing the plasma level of lysophosphatidic acid. In some embodiments, the individual has a metabolic disorder and the metabolic disorder is treated by improving glucose tolerance. In some embodiments, the subject does not have a metabolic disorder. In some embodiments, the autotaxin inhibitor delays or prevents the onset of a metabolic disorder in an individual by improving glucose tolerance.

In some embodiments, described herein is a method for decreasing adipose tissue expansion in a subject comprising administering to the subject an autotaxin inhibitor. In studies of heterozygous autotaxin deficient transgenic mice, control mice (homozygous autotaxin mice) fed a high fat diet have higher weight gains than the heterozygous deficient transgenic mice, despite no change in food intake. Also, the autotaxin deficiency in the transgenic mice similarly suppress adipose mass expansion, improved metabolism, and had less inflammation when compared to control mice also fed a high fat diet.

In some embodiments, described herein is a method of treatment of a metabolic disorder in a subject that is overweight or obese. In some embodiments, an autotaxin inhibitor is used to treat obesity in a subject. In some embodiments, the autotaxin inhibitor decreases adipose tissue expansion in the subject that is overweight or obese. In some embodiments, the metabolic disorder is treated by decreasing adipose tissue expansion.

In some embodiments, administration of an autotaxin inhibitor to a subject delays or prevents the onset of a metabolic disorder by decreasing adipose tissue expansion. In some embodiments, the subject is at risk for developing a metabolic disorder.

Drug Induced Hyperglycemia

In some embodiments, administration of an autotaxin inhibitor to a subject treats, prevents, or ameliorates the symptoms of drug induced hyperglycemia. In some embodiments, administration of an autotaxin inhibitor to a subject treats, prevents, or ameliorates the symptoms of drug induced hyperglycemia by reducing blood glucose levels. Pharmacological agents can affect glucose homestasis that can result in hyperglycemia. In some embodiments, the hyperglycemia occurs in the absence of a diagnosis of diabetes. If left untreated, the elevated blood glucose levels can lead to a medical emergency. Symptoms include, but are not limited to fatigue, weakness, fruity odor of the breath, confusion, lack of concentration, shortness of breath, nausea, vomiting, dry skin, and flushing of the skin. Common drug categories that are associated with contributing to hyperglycemia include, but are not limited to: antibiotics, such as fluoroquinolones including gatifloxacin; beta-blockers, such as propranolol, metoprolol or atenolol; thiazide, such as hydrochlorothiazide, and thiazide-like diuretics, and thiazide-like drugs (metolazone); second-generation antipsychotics (SGAs) or "atypical antipsychotics" such as olanzapine or clozapine; corticosteroids; calcinuerin inhibitors such as cyclosporine, sirolimus or tarcrolimus; protease inhibitors such as ritonavir.

Stress Induced Hyperglycemia

In some embodiments, administration of an autotaxin inhibitor to a subject treats or prevents or delays the onset of stress induced hyperglycemia. In some embodiments, administration of an autotaxin inhibitor to a subject treats or prevents or delays the onset of stress induced hyperglycemia by reducing blood glucose levels. Stressed induced hyperglycemia (SIH) is a transient increase in plasma glucose levels higher than 200 mg/dL which occurs during an acute illness or injury. In some embodiments, the hyperglycemia occurs in the absence of a diagnosis of diabetes. The SIH results from an excess of glucose production relative glucose clearance. SIH has been associated with conditions including, but not limited to, myocardial infarction, stroke, and trauma. SIH has been associated with increase mortality and a higher incidence of congestive heart failure and cardiogenic shock in patients after myocardial infarction. Stroke victims have higher mortality associated with SIH and worse odds of desirable neurological outcomes as glucose levels increase with SIH. Hyperglycemia was also shown to be a predictor of infectious complications in the form of pneumonia, urinary tract infections, wound infections and bacteria. Overall, published studies have consistently shown higher morbidity and higher mortality rates in those patients that present with SIH.

Methods of Treating, Delaying, and/or Preventing the Onset of a Metabolic Disorder with an Autotaxin Inhibitor In certain embodiments, the methods provided herein comprise measuring blood glucose levels. Blood glucose levels may be measured before and/or after administration of an autotaxin inhibitor. Blood glucose levels may be measured in whole blood, or may be measured in plasma. Blood glucose levels may be measured in a clinical laboratory, or may be measured using a blood glucose meter.

In certain embodiments, blood glucose levels are measured in a subject when the subject has fasted for at least 8 hours. In certain embodiments, blood glucose levels are measured at random times, and the measurement is not timed according to the intake of food or drink. In certain embodiments, blood glucose levels are measured in the post-prandial state, i.e. after the subject has eaten a meal. In certain embodiments, blood glucose levels are measured in a subject two hours after the subject has eaten a meal. In certain embodiments, blood glucose levels are measured at timed intervals following administration of glucose to the subject, in order to determine how quickly the subject's body clears glucose from the blood. Any measurements of blood glucose levels may be made in whole blood or in plasma.

In certain embodiments, the subject has elevated blood glucose levels. In certain embodiments, a subject is identified as having elevated blood glucose levels. Such identification is typically made by a medical professional. In certain embodiments, an elevated blood glucose level is a fasting blood glucose level between 100 and 125 mg/dL. In certain embodiments, an elevated blood glucose level is a fasting blood glucose level above 126 mg/dL. In certain embodiments, an elevated blood glucose level is a two-hour post-prandial glucose level between 140 and 199 mg/dL. In certain embodiments, an elevated blood glucose level is a two-hour post-prandial glucose level at 200 mg/dL or higher.

In certain embodiments, a subject having elevated blood glucose levels has pre-diabetes. In certain embodiments, a subject is identified as having pre-diabetes. In certain such embodiments, the subject has a fasting blood glucose level between 100 and 125 mg/dL. In certain such embodiments, the subject has a two-hour post-prandial blood glucose level between 140 and 199 mg/dL. A diagnosis of pre-diabetes is typically made by a medical professional, who may consider factors in addition to blood glucose levels when determining whether a subject has pre-diabetes.

In certain embodiments, a subject having elevated blood glucose levels has diabetes. In certain embodiments, a subject is identified as having diabetes according to the subject's blood glucose levels. In certain such embodiments, the subject has a fasting blood glucose level above 126 mg/dL. In certain such embodiments, the subject has a two-hour post-prandial blood glucose level at or above 200 mg/dL. A diagnosis of diabetes is typically made by a medical professional, who may consider factors in addition to blood glucose levels when determining whether a subject has diabetes.

In certain embodiments, the methods provided herein comprise monitoring blood glucose levels before administration of an autotaxin inhibitor. In certain embodiments, the methods provided herein comprise measuring blood glucose levels after administration of an autotaxin inhibitor. In certain embodiments, a subject measures blood glucose levels one or more times daily.

In certain embodiments, methods for reducing blood glucose levels comprise reducing a subject's blood glucose levels to blood glucose levels determined as desirable by medical organizations, such as the American Diabetes Association or the World Health Organization. In certain embodiments, blood glucose levels are reduced below 130 mg/dL when measured before a subject has had a meal. In certain embodiments, blood glucose levels are reduced to below 180 mg/dL when measured after a subject has had a meal.

Measurements of HbA1c levels may be used to determine how well a subject's blood glucose levels are controlled over time. HbA1c levels are an indication of the amount of glycated hemoglobin in the blood, and can provide an estimate of how well a subject's blood glucose levels have been managed over 2-3 month period prior to the measurement of HbA1c levels. High HbA1c levels may put a subject at risk for developing complications related to diabetes, such as eye disease, heart disease, kidney disease, nerve damage, or stroke. As such, in certain embodiments it is desirable that a subject's HbA1c levels be within ranges that are considered normal by a medical professional. In certain embodiments, an HbA1c level of 6% or less is normal. In certain embodiments, a medical professional may recommend that a subject's HbA1c level be 7% or less. In certain embodiments, the administering results in reduced HbA1c levels.

Also described herein are methods for reducing blood glucose levels by administering an autotaxin inhibitor to a subject with elevated blood glucose levels relative to a control. In some embodiments, a control is the blood glucose levels of an individual without a metabolic disorder. In some embodiments, a control is a blood glucose level lower than 100 mg/dL. In some embodiments, the autotaxin inhibitor is used to treat an underlying metabolic disorder. In some embodiments, the metabolic disorder is treated by reducing blood glucose levels by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 45%, and 50%. In some embodiments, the blood glucose level is reduced to below 200 mg/dL. In certain embodiments, the blood glucose level is reduced to below 175 mg/dL. In certain embodiments, the blood glucose level is reduced to below 150 mg/dL. In certain embodiments, the blood glucose level is reduced to below 125 mg/dL. In certain embodiments, the blood glucose level is reduced to below 120 mg/dL. In certain embodiments, the blood glucose level is reduced to below 115 mg/dL. In certain embodiments, the blood glucose level is reduced to below 110 mg/dL. In certain embodiments, the blood glucose level is reduced to below 105 mg/dL. In certain embodiments, the blood glucose level is reduced to below 100 mg/dL.

In some embodiments, the subject is overweight or obese. In some embodiments, the subject has type 2 diabetes. In some embodiments, the subject has metabolic syndrome. In some embodiments, the subject has non-alcoholic fatty liver disease and/or nonalcoholic steatohepatitis.

In some embodiments, the subject does not have a metabolic disorder. In some embodiments, the autotaxin inhibitor delays or prevents the onset of the metabolic disorder by reducing elevated blood glucose levels relative to a control. In some embodiments, a control is a blood glucose level lower than 110 mg/dL. In some embodiments, the elevated blood glucose levels are reduced by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 45%, and 50%. In some embodiments, the blood glucose level is reduced to below 200 mg/dL. In certain embodiments, the blood glucose level is reduced to below 175 mg/dL. In certain embodiments, the blood glucose level is reduced to below 150 mg/dL. In certain embodiments, the blood glucose level is reduced to below 125 mg/dL. In certain embodiments, the blood glucose level is reduced to below 120 mg/dL. In certain embodiments, the blood glucose level is reduced to below 115 mg/dL. In certain embodiments, the blood glucose level is reduced to below 110 mg/dL. In certain embodiments, the blood glucose level is reduced to below 105 mg/dL. In certain embodiments, the blood glucose level is reduced to below 100 mg/dL.

Also described herein are methods for reducing plasma lysophosphatidic acid levels in an individual by administering an autotaxin inhibitor. In some embodiments, the plasma lysophosphatidic acid levels in the individual are elevated relative to a control. In some embodiments, the plasma lysophosphatidic acid levels of the control are at least 1.2 mM or lower. In some embodiments, the control is the lysophosphatidic acid levels of an individual without a metabolic disorder. In some embodiments, the elevated plasma lysophosphatidic acid concentrations in the individual contribute to or increase the risk for developing a metabolic disorder.

Accordingly, the methods disclosed herein comprise administering an autotaxin inhibitor to an individual with elevated lysophosphatidic acid levels to treat an underlying metabolic disorder. In some embodiments, the metabolic disorder is treated by reducing plasma lysophosphatidic acid levels with an autotaxin inhibitor. In some embodiments, the lysophosphatidic acid levels are reduced by the autotaxin inhibitor by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 45%, and 50%. In some embodiments, the subject has decreased insulin sensitivity. In some embodiments, insulin sensitivity in the subject is improved by decreasing plasma lysophosphatidic acid levels. In some embodiments, the subject has elevated blood glucose levels relative to a control. In some embodiments, a control is the blood glucose levels of an individual without a metabolic disorder. In some embodiments, the elevated blood glucose levels are reduced by reducing lysophosphatidic acid levels.

In some embodiments, the subject does not have a metabolic disorder. In some embodiments, the autotaxin inhibitor delays or prevents the onset of the metabolic disorder by reducing plasma lysophosphatidic acid levels by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 45%, and 50%.

Provided herein are methods for improving insulin sensitivity in a subject comprising administering to the subject an autotaxin inhibitor; and thereby improving insulin sensitivity in the subject. In certain embodiments, the subject has insulin resistance. In some embodiments, the individual with insulin resistance has fasting insulin levels of at least 20 μU/mL. In some embodiments, the individual with insulin resistance has fasting insulin levels that exceed 100 μU/mL. In some embodiments, the autotaxin inhibitor treats a metabolic disorder by improving insulin resistance. In some embodiments, the autotaxin inhibitor treats a metabolic disorder by improving insulin sensitivity. In certain embodiments, the methods comprise selecting a subject having insulin resistance.

Provided herein are methods for preventing or delaying the onset of insulin resistance in a subject at risk for developing insulin resistance comprising administering to the subject an autotaxin inhibitor; and thereby preventing or delaying the onset of insulin resistance in the subject. In certain embodiments, the methods comprise selecting a subject at risk for developing insulin resistance.

In some embodiments, the autotaxin inhibitor improves insulin secretion by decreasing the level of lysophosphatidic acid. In some embodiments, a metabolic disorder is treated by increasing insulin secretion. In some embodiments, the subject does not have a metabolic disorder. In some embodiments, the autotaxin inhibitor delays or prevents the onset of the metabolic disorder by increasing insulin secretion.

In some embodiments, described herein is a method of improving glucose tolerance in an individual comprising administering an autotaxin inhibitor to the subject with impaired glucose tolerance. In some embodiments, the autotaxin inhibitor improves glucose tolerance in the individual by decreasing the level of lysophosphatidic acid. In some embodiments, the individual has a metabolic disorder and the metabolic disorder is treated by improving glucose tolerance. In some embodiments, the subject does not have a metabolic disorder. In some embodiments, the autotaxin inhibitor delays or prevents the onset of a metabolic disorder in an individual by improving glucose tolerance.

In some embodiments, described herein is a method for decreasing adipose tissue expansion in a subject comprising administering to the subject an autotaxin inhibitor.

In some embodiments, described herein is a method of treatment a metabolic disorder in a subject that is overweight or obese. In some embodiments, an autotaxin inhibitor is used to treat obesity in a subject. In some embodiments, the autotaxin inhibitor decreases adipose tissue expansion in the subject that is overweight or obese. In some embodiments, the metabolic disorder is treated by decreasing adipose tissue expansion.

In some embodiments, administration of an autotaxin inhibitor to a subject delays or prevents the onset of a metabolic disorder by decreasing adipose tissue expansion. In some embodiments, the subject is at risk for developing a metabolic disorder.

Certain Terminology

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

"Blood glucose level" means the concentration of glucose in the blood of a subject. In certain embodiments, blood glucose levels are expressed as milligrams of glucose per deciliter of blood. In certain embodiments, blood glucose levels are expressed as mmol of glucose per liter of blood.

"Elevated blood glucose level" means a blood glucose level that is higher than normal.

"Fasted blood glucose level" means a blood glucose level after a subject has fasted for a certain length of time. For example, a subject may fast for at least 8 hours prior to measurement of a fasted blood glucose level.

"Post-prandial blood glucose level" means a blood glucose level after a subject has eaten a meal. In certain embodiments, a post-prandial blood glucose level is measured two hours after a subject has eaten a meal.

"Plasma blood glucose level" means the concentration of glucose in plasma following separation of whole blood into plasma and red blood cell fractions.

"Plasma lysophosphatidic acid level" means the concentration of lysophosphatidic acid in plasma following separation of whole blood into plasma and red blood cell fractions.

"Impaired glucose intolerance" is defined as a two-hour glucose levels (glycemia) of about 140 to about 199 mg/dL (7.8 to 11.0 mmol) on the 75-g oral glucose tolerance test (according to WHO and ADA).

"Insulin sensitivity" means the ability of cells to take up glucose in response to insulin action.

"Insulin resistance" means a condition in which normal amounts of insulin are inadequate to produce a normal insulin response from fat, muscle and liver cells. Insulin resistance in fat cells results in hydrolysis of stored triglycerides, which elevates free fatty acids in the blood. Insulin resistance in muscle reduces the uptake of glucose from the blood by muscle cells. Insulin resistance in liver reduces glucose storage and a failure to suppress glucose production. Elevated free fatty acids, reduced glucose uptake, and elevated glucose production all contribute to elevated blood glucose levels. High plasma levels of insulin and glucose due to insulin resistance often leads to metabolic syndrome and type 2 diabetes.

"Improving insulin resistance" means increasing the ability of cells to produce a normal insulin response. In certain embodiments, insulin resistance is improved in muscle cells, leading to an increased uptake of glucose in muscle cells. In certain embodiments, insulin resistance is improved in liver cells, leading to increased glucose storage in liver cells. In certain embodiments, insulin resistance is improved in fat cells, leading to reduced hydrolysis of triglycerides, and consequently reduced free fatty acid in the blood.

"Adipose tissue expansion" means an increase in the size of adipose cells compared to the normal size of adipose cells. In certain embodiments, the adipose tissue expansion is due to a high fat diet consumed by the subject.

"Hypoglycemia" refers to a condition in which the blood glucose level is too low. Typically, hypoglycemia occurs when the blood glucose level falls below 70 mg/dl in an individual.

"Prediabetes" means a condition in which a subject's blood glucose levels are higher than in a subject with normal blood glucose levels but lower but not high enough for a diagnosis of diabetes. Typically, A1C levels are at least 6.0% or greater. Typically, fasting plasma glucose levels are at least 5.6 mmol/L (100 mg/dL) or greater.

"Type 1 diabetes" means diabetes characterized by loss of the insulin-producing beta cells of the islets of Langerhans in the pancreas leading to a deficiency of insulin (also known as insulin-dependent diabetes mellitus or IDDM). Type I diabetes can affect children or adults, but typically appears between the ages of 10 and 16.

"Type 2 diabetes" means diabetes characterized by insulin resistance and relative insulin deficiency (also known as diabetes mellitus type 2, and formerly called diabetes mellitus type 2, non-insulin-dependent diabetes (NIDDM), obesity related diabetes, or adult-onset diabetes).

"Obesity" means an excessively high amount of body fat or adipose tissue in relation to lean body mass. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

"Metabolic syndrome" means a condition characterized by a clustering of lipid and nonlipid risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Non-alcoholic fatty liver disease (NAFLD)" refers to a fatty liver disease that occurs when fat is deposited in the liver not due to excessive alcohol use.

"Nonalcoholic steatohepatitis (NASH)" refers to a liver inflammation caused by a buildup of fat in the liver that is not due to alcohol abuse "Subject" or "individual" means a mammal. In some embodiments, the mammal is a human.

The terms "administer," "administering", "administration," and the like, as used herein, refer to the methods that may be used to enable delivery of compounds or compositions to the desired site of biological action. These methods include, but are not limited to oral routes of administration, intraduodenal routes of administration, parenteral injection (including intravenous, subcutaneous, intraperitoneal, intramuscular, intravascular or infusion), topical and rectal administration. Any suitable route of administration of the autotaxin inhibitors described herein is contemplated. In some embodiments, the compounds and compositions described herein are administered orally.

"At risk for developing" means a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

Autotaxin Inhibitors

In some embodiments, an autotaxin inhibitor contemplated for use in any of the embodiments described herein is: a protein, a peptide, a polypeptide, a peptidomimetic, an antibody, a small molecule, a small interfering RNA-encoding polynucleotide, an antisense RNA-encoding polynucleotide, or a ribozyme-encoding polynucleotide. In some embodiments, the autotaxin inhibitor is an antibody to autotaxin.

Small Molecule Autotaxin Inhibitors:

In some embodiments, the autotaxin inhibitor contemplated for use in any of the embodiments described herein is a small molecule inhibitor.

In some embodiments, the autotaxin inhibitor is a small molecule inhibitor that is characterized as having one or more of the following properties:

a molecular weight of at most 700 capability of at least 50% inhibition (at 1 micromolar) of autotaxin conversion of lysophosphatidyl choline to lysophosphatidic acid in a suitable in vitro assay that measures such activity selective inhibition of autotaxin activity suitable for administration to human at therapeutically relevant doses with at least 50% inhibition of autotaxin at trough In some embodiments, the autotaxin inhibitor is a small molecule heterocyclic compound. In some embodiments, the autotaxin inhibitor is a small molecule indole derivative. In some embodiments, the autotaxin inhibitor is small molecule tetracyclic compound. In some embodiments, the autotaxin inhibitor is small molecule piperidine or piperazine containing compound. In some embodiments, the autotaxin inhibitor is a small molecule benzonaphtyridine derivative. In some embodiments, the autotaxin inhibitor is a small molecule pyrimidine derivatives. In some embodiments, the autotaxin inhibitors are imidazole derivatives. In some embodiments, the autotaxin inhibitors are bicyclic derivatives. In some embodiments, the autotaxin inhibitors are diazaspirocycloalkane or azaspirocycloalkane derivatives. In some embodiments, the autotaxin inhibitors are pyridazine derivatives. In some embodiments, the autotaxin inhibitors are pyrimidine and pyridine derivatives. In some embodiments, the autotaxin inhibitors are pipemidic acid derivatives. In some embodiments, the autotaxin inhibitors are thiazole derivatives.

In some embodiments, the autotaxin inhibitor is a compound of Formula (I), or a pharmaceutically acceptable salt or solvate thereof, as described in U.S. Provisional Application No. 61/883,026 (filed on Sep. 26, 2013):

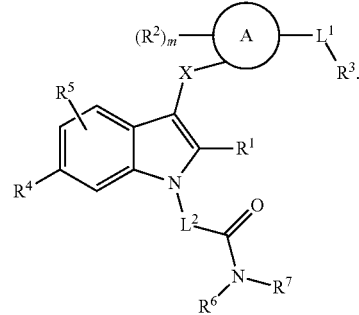

Formula (I)

In other embodiments, the autotaxin inhibitor is a compound as described in Tables 1-4 of U.S. Provisional Application No. 61/883,026. In other embodiments, the autotaxin inhibitor is a compound having the structure A1, A2, A3, A4, or A5 as described in Paragraph [00244] of U.S. Provisional Application No. 61/883,026. In other embodiments, the autotaxin inhibitor is a compound of any one of Examples 1-79 as described in U.S. Provisional Application No. 61/883,026.

In some embodiments, the autotaxin inhibitor has the following structure:

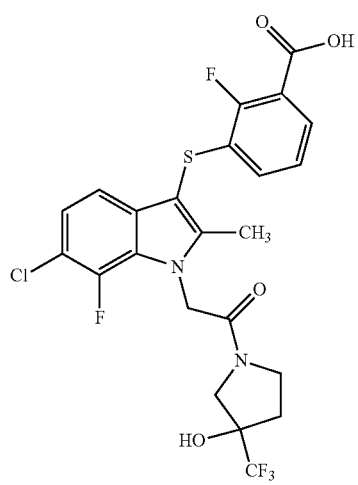

Compound E

In some embodiments, Compound E is used as the sodium salt.

In some embodiments Compound E is used in racemic form. In some embodiments the R-enantiomer of Compound E is used. In some embodiments the S-enantiomer of Compound E is used.

In some embodiments, the autotaxin inhibitor is a compound of Formula (I), or pharmaceutically acceptable salt, pharmaceutically acceptable solvate or prodrug thereof, as described in U.S. Provisional Application No. 61/878,922 (filed on Sep. 17, 2013):

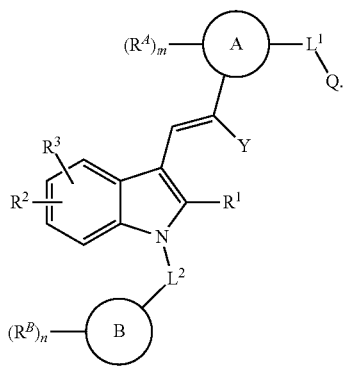

Formula (I)

In other embodiments, the autotaxin inhibitor is a compound as described in Table 1 or 2 of U.S. Provisional Application No. 61/878,922. In other embodiments, the autotaxin inhibitor is a compound as described in any one of Examples 1-41 in U.S. Provisional Application No. 61/878,922.

In some embodiments, the autotaxin inhibitor is a compound of Formula (I), or a pharmaceutically acceptable salt or solvate thereof, as described in U.S. Provisional Application No. 61/907,947 (filed on Nov. 22, 2013):

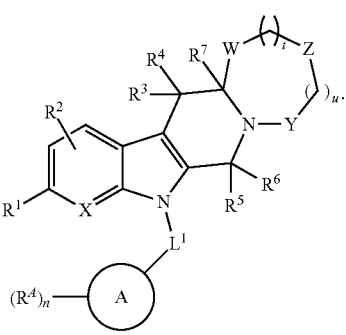

Formula (I)

In other embodiments, the autotaxin inhibitor is a compound as described in Paragraph [00116], [00117], [00122], [00123], [00125], [00126], [00128], [00129], [00131] or [00132] of U.S. Provisional Application No. 61/907,947. In other embodiments, the autotaxin inhibitor is a compound as described in Table 1, 2, or 3 of U.S. Provisional Application No. 61/907,947. In other embodiments, the autotaxin inhibitor is a compound as described in any one of Examples 1-13 of U.S. Provisional Application No. 61/907,947.

In some embodiments, the autotaxin inhibitor has the following structure:

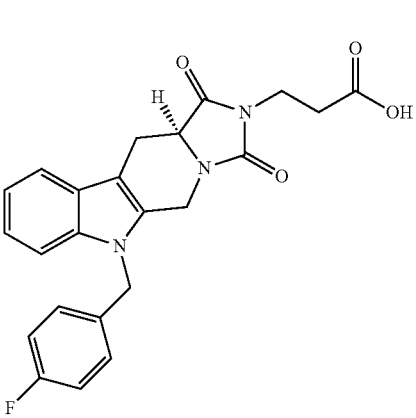

Compound A

In some embodiments, Compound A is used as the sodium salt.

In some embodiments Compound A is used in racemic form. In some embodiments, the R-enantiomer of Compound A is used. In some embodiments the S-enantiomer of Compound A is used.

In some embodiments, the autotaxin inhibitor is a compound of Formula (I), or a pharmaceutically acceptable salt, pharmaceutically acceptable solvate, or prodrug thereof, as described in U.S. Provisional Application No. 61/878,945 (filed on Sep. 17, 2013):

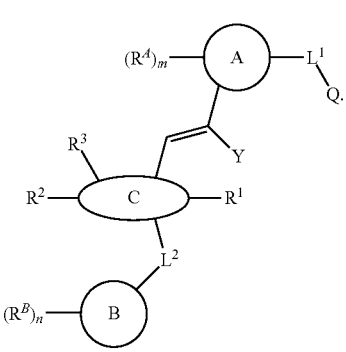

Formula (I)

In other embodiments, the autotaxin inhibitor is a compound as described in Table 1, 2, 3, 4, 5, or 6 of U.S. Provisional Application No. 61/878,945. In other embodiments, the autotaxin inhibitor is a compound as described in any one of Examples 1-13 of U.S. Provisional Application No. 61/878,945.

In some embodiments, the autotaxin inhibitor is a compound of Formula (I), or a pharmaceutically acceptable salt, or solvate thereof as described in U.S. Provisional Application No. 61/907,965 (filed on Nov. 22, 2013):

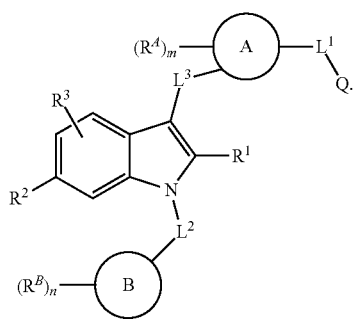

Formula (I)

In other embodiments, the autotaxin inhibitor is a compound as described in Paragraph of U.S. Provisional Application No. 61/907,965. In other embodiments, the autotaxin inhibitor is a compound as described in any one of Examples 1-8 of U.S. Provisional Application No. 61/907,965.

In some embodiments, the autotaxin inhibitor has one of the following structures:

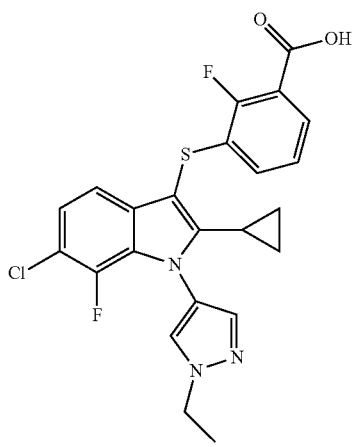

Compound B

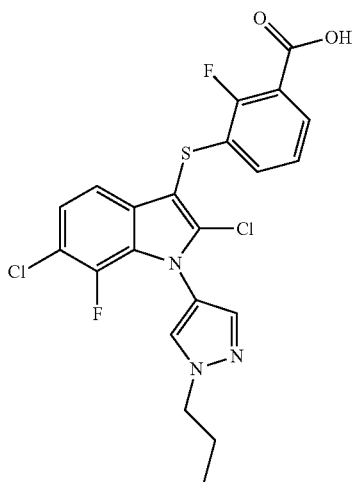

Compound C

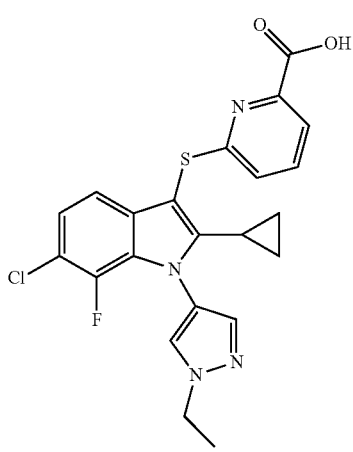

Compound D

In some embodiments, Compound B is used as the sodium salt. In some embodiments, Compound C is used as the sodium salt. In some embodiments, Compound D is used as the sodium salt.

In some embodiments, the autotaxin inhibitor is a compound of Formula (I), or a pharmaceutically acceptable salt, or pharmaceutically acceptable solvent or prodrug thereof as described in WO 2012/166415 (published on Dec. 6, 2012):

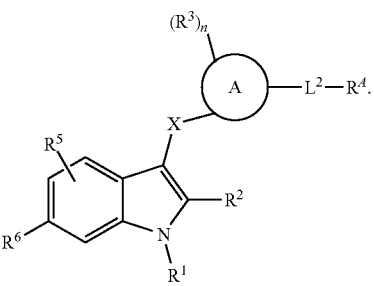

Formula (I)

In other embodiments, the autotaxin inhibitor is a compound as described in Table 1 of WO 2012/166415. In other embodiments, the autotaxin inhibitor is a compound as described in any one of Examples 1-18 of WO 2012/166415.

In some embodiments, the autotaxin inhibitor is a compound of Formula (I), or a pharmaceutically acceptable salt, or pharmaceutically acceptable solvent or prodrug thereof as described in WO 2012/024620 (published on Feb. 23, 2012):

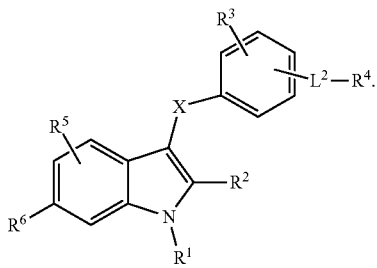

Formula (I)

In other embodiments, the autotaxin inhibitor is a compound as described in Table 1, 2, 3 or 4 of WO 2012/024620. In other embodiments, the autotaxin inhibitor is a compound as described in any one of Examples 1-157 of WO 2012/024620.

In some embodiments, the autotaxin inhibitor is a compounds of Formula I as described in WO 2009/046841 (published on Apr. 16, 2009):

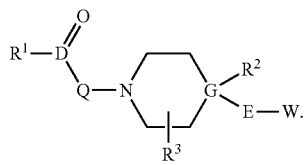

Formula I

In other embodiments, the autotaxin inhibitor is a compound described in the table on pages 65-101 in WO 2009/046841. In other embodiments, the autotaxin inhibitor is a compound described in the table on pages 104-106 of WO 2009/046841.

In some embodiments, the autotaxin inhibitor is a compound of Formula I as described in WO 2010/060532 (published on Jun. 3, 2010):

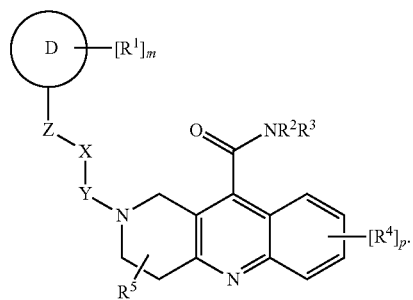

Formula I

In other embodiments, the autotaxin inhibitor is the compound of Example 1 ("A1") as described in WO 2010/060532. In other embodiments, the autotaxin inhibitors is a compound described on pages 49-108 of WO 2010/060532.

In some embodiments, the autotaxin inhibitor is a compound of Formula I as described in WO 2011/006569 (published on Jan. 20, 2011):

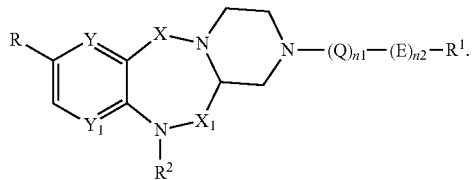

Formula I

In other embodiments, the autotaxin inhibitor is compound A173 of Example 18 as described in WO 2011/006569. In other embodiments, the autotaxin inhibitor is a compound as described on pages 69-141 of WO 2011/006569.

In some embodiments, the autotaxin inhibitor is a compound of Formula Ia, Ib, and II as described in WO 2010/115491 (published on Oct. 14, 2010):

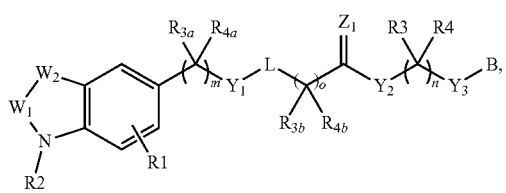

Formula Ia

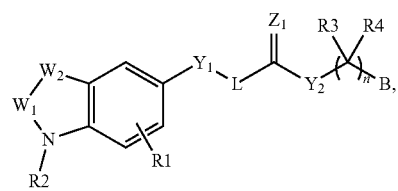

Formula Ib and

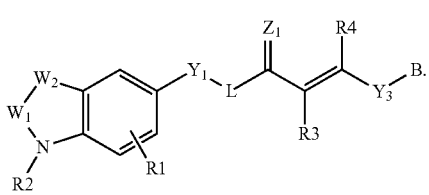

Formula II

In other embodiments, the autotaxin inhibitor is Compound 1 as described in WO 2010/115491. In other embodiments, the autotaxin inhibitors are the compounds of Table 2 as described in WO 2010/115491.

In some embodiments, the autotaxin inhibitor is a compound of Formula I as described in WO 2010/063352 (published on Jun. 10, 2010):

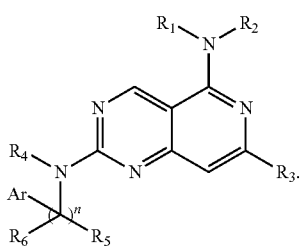

Formula I

In other embodiments, the autotaxin inhibitor is Compound 8 as described in WO 2010/063352. In other embodiments, the autotaxin inhibitors are the compounds of 1-157 as described in WO 2010/063352. In other embodiments, the autotaxin inhibitor is a compound as described in Table 2 of WO 2010/063352.

In some embodiments, the autotaxin inhibitor is a compound of Formula I as described in WO 2009/046804 (published on Apr. 16, 2009):

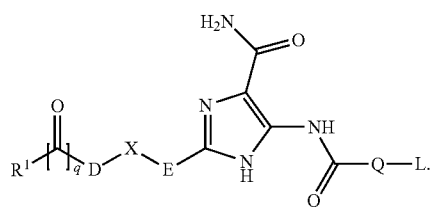

Formula I

In other embodiments, the autotaxin inhibitor is compound A2 as described in WO 2009/046804. In other embodiments, the autotaxin inhibitor is a compound as described on pages 64-115 of WO 2009/046804.

In some embodiments, the autotaxin inhibitor is a compound of Formula I, or a pharmaceutically acceptable salt thereof, as described in WO 2014/097151 (published on Jun. 26, 2014):

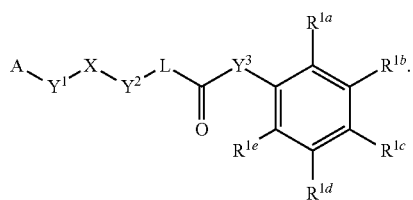

Formula I

In other embodiments, the autotaxin inhibitor is embodiment 27 (page 37) as described in WO 2014/09151. In other embodiments, the autotaxin inhibitor is a compound as described in any one of Examples 1-75 of WO 2014/097151.

In some embodiments, the autotaxin inhibitor is a compound of Formula I, or a pharmaceutically acceptable salt thereof, as described in WO 2014/048865 (Published Apr. 3, 2014):

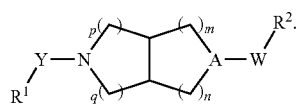

Formula I

In other embodiments, the autotaxin inhibitor is a compound as described in the tables on pages 85-256 of WO 2014/048865. In other embodiments, the autotaxin inhibitor is a compound as described in any one of Examples 1-44 of WO 2014/048865.

In some embodiments, the autotaxin inhibitor is a compound of Formula I, or a pharmaceutically acceptable salt thereof, as described in WO 2013/186159 (published on Dec. 19, 2013):

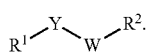

Formula I

In other embodiments, the autotaxin inhibitor is a compound as described in Table 1, 2, 3, 4, 5, 6, or 7 of WO 2013/186159. In other embodiments, the autotaxin inhibitor is a compound as described in any one of Examples 1-16 of WO 2013/186159. In other embodiments, the autotaxin inhibitor is a compound as described in the table on pages 89-95 of WO 2013/186159.

In some embodiments, the autotaxin inhibitor is a compound of Formula I, or a pharmaceutically acceptable salt thereof, as described in WO 2013/061297 (published on May 2, 2013):

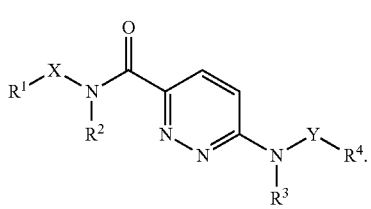

Formula I

In other embodiments, the autotaxin inhibitor is a compound as described in Table 1 of WO 2013/061297. In other embodiments, the autotaxin inhibitor is a compound as described in any one of Examples 1-14 of WO 2013/061297.

In some embodiments, the autotaxin inhibitor is a compound of Formula I, or a pharmaceutically acceptable salt thereof, as described in WO 2013/054185 (published on Apr. 18, 2013):

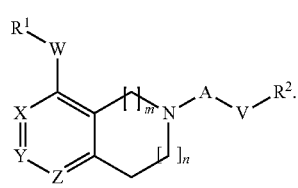

Formula I

In other embodiments, the autotaxin inhibitor is a compound described in Table 1 of WO 2013/054185. In other embodiments, the autotaxin inhibitor is a compound as described in any one of Example Number 1-53 of WO 2013/054185.

In some embodiments, the autotaxin inhibitor is a compound as described in U.S. Pat. No. 8,268,891 (issued on Sep. 18, 2012; U.S. application Ser. No. 12/270,840). In some embodiments, the autotaxin inhibitor is compound 7905958, 5186522, 7839888, 5761473, 5564949, 5538444, 5711925, 5564676, 7921385, or 5210574 as described in U.S. Pat. No. 8,268,891.

In some embodiments, the autotaxin inhibitor is a compound as described in U.S. Pat. No. 8,497,371 (issued on Jul. 30, 2013; U.S. patent application Ser. No. 12/912,604). In other embodiments, the autotaxin inhibitor is a compound as described in any one of Examples 1-31 of U.S. Pat. No. 8,497,371.

In some embodiments, the autotaxin inhibitor is a compound of Formula Ia-Im as described in WO 2011/044978 (published on Apr. 21, 2011). In other embodiments, the autotaxin inhibitor is a compound described on pages 36-42 of WO 2011/044978.

In some embodiments, the autotaxin inhibitor is a compound of Formula I as described in WO 2010/112116 (published on Oct. 7, 2010):

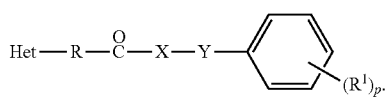

Formula I

In other embodiments, the autotaxin inhibitor is a compound as described in any one of Examples 1-11 of WO 2010/112116. In other embodiments, the autotaxin inhibitor is compound described in the table on pages 63-69 of WO 2010/112116.

In some embodiments, the autotaxin inhibitor is a compound of Formula I as described in WO 2009/046842 (published on Apr. 16, 2009):

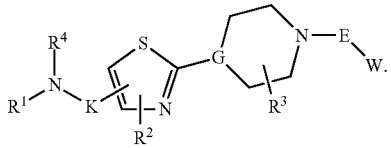

Formula I

In other embodiments, the autotaxin inhibitor is a compound as described in any one of the tables on pages 56-72 of WO 2009/046842.

In some embodiments, the autotaxin inhibitor is a boronic acid based compound. In some embodiments, the autotaxin inhibitors is HA155, HA130, or E-HA219. Boronic acid based autotaxin inhibitors, include and are not limited to those disclosed in H. M. Albers et al., J. Med. Chem. 2011, 54, 4619-4626; H. M. Albers et al., J. Med. Chem. 2010, 53, 4958-4967; and H. M. Albers et al., Proc. Natl. Acad. Sci. USA 2010, 107, 7257-7262.

Other autotaxin inhibitors contemplated for use include but are not limited to PF-8380, vinpocetin, damnacanthal, NSC-48300, NSC-9616, H2L-7905958, bithionol, NSC 12859, NSC 75779, NSC 5014, NSC 341348, NSC 75520, hexachlorophene, merbromin, eosin Y and 2,2'-methylenebis(4-chlorophenol). In other embodiments, the autotaxin inhibitors are the compounds as described in J. Gierse et al., J. Pharmacol. Exp. 2010, 334, 310-317; N. Moulharat et al., Chem.-Biol. Interact. 2008, 172, 115-124; L. P. Saunders et al., Mol. Cancer. Ther. 2008, 7, 3352-3362; WO 2009/151644 (published on Dec. 17, 2009); E. J. North et al., J. Med. Chem. 2010, 53, 3095-3105; A. Parrill et al., Bioorg. Med. Chem. 2008, 16, 1784-1795; A. Hoeglund et al., J. Med. Chem. 2010, 53, 1056-1066; A. B. Hoeglund et al., Bioorg. Med. Chem. 2010, 18, 769-776; US 2014/0171404 (published on Jun. 19, 2014; U.S. patent application Ser. No. 14/109,935); US 2014/0171403 (published on Jun. 19, 2014; U.S. patent application Ser. No. 13/833,460); US 2013/012505 (published on Jan. 10, 2013; U.S. patent application Ser. No. 13/637,161); WO 2011/053597 (published on May 5, 2011); US 2012/0100592 (published on Apr. 26, 2012; U.S. patent application Ser. No. 12/912,604); US 2012/0202827 (published on Aug. 9, 2012; U.S. patent application Ser. No. 13/501,467); U.S. Pat. No. 8,552,001 (issued on Oct. 8, 2013; U.S. patent application Ser. No. 13/501,467); US 2012/0115852 (published on May 10, 2012; U.S. patent application Ser. No. 13/383,908); WO 2011/116867 (published on Sep. 29, 2011); US 2013/0012505 (published on Jan. 10, 2013; WO 2011/002918 (published on Jan. 6, 2011); U.S. patent application Ser. No. 13/637,161); US 2011/0160148 (published on Jun. 30, 2011; U.S. patent application Ser. No. 12/828,053); U.S. Pat. No. 8,343,934 (issued on Jan. 1, 2013; U.S. patent application Ser. No. 12/828,053); US 2012/0059016 (published on Mar. 8, 2012; U.S. patent application Ser. No. 13/258,068); US 2012/0015976 (published on Mar. 9, 2010; U.S. application Ser. No. 13/258,077); U.S. Pat. No. 8,329,907 (issued on Dec. 11, 2012; U.S. patent application Ser. No. 13/258,077); US 2012/0015959 (published on Jan. 19, 2012; U.S. patent application Ser. No. 13/259,464); US 2011/0237583 (published on Sep. 29, 2011; U.S. patent application Ser. No. 13/132,181); U.S. Pat. No. 8,530,650 (issued on Sep. 10, 2013; U.S. patent application Ser. No. 13/132,181); US 2011/0230471 (published on Sep. 22, 2011; U.S. patent application Ser. No. 13/131,696) WO 2010/112124 (published on Oct. 7, 2010); US 2011/0110886 (published on May 12, 2011; U.S. patent application Ser. No. 12/993,397); US 2010/0222341 (published Sep. 2, 2010; U.S. patent application Ser. No. 12/681,440); US 2010/0249132 (published on Sep. 30, 2010; U.S. patent application Ser. No. 12/681,380); US 2010/0240676 (published on Sep. 23, 2010; U.S. patent application Ser. No. 12/681,724); U.S. Pat. No. 8,557,824 (issued on Oct. 15, 2011; U.S. patent application Ser. No. 12/681,724); US 2013/0029948 (published on Jan. 31, 2013; U.S. patent application Ser. No. 13/476,607); US 2013/0150326 (published on Jun. 13, 2013; U.S. patent application Ser. No. 13/817,968) and US 2014/0200231 (published on Jul. 17, 2014; U.S. patent application Ser. No. 14/148,775); all of which are incorporated by reference for the disclosure of such compounds.

Lipid-based ATX Inhibitors:

In some embodiments, the autotaxin inhibitors are compounds that are lipids or lipid based. In some embodiments, the autotaxin inhibitor is lysophosphatic acid (LPA). In some embodiments, the autotaxin inhibitor is sphingosine 1-phosphate (S1P). In some embodiments, the autotaxin inhibitors are LPA or S1P analogs. In some embodiments, the autotaxin inhibitors are phosphates analogs. In some embodiments, the autotaxin inhibitors are phosphonates analogs. In some embodiments, the autotaxin inhibitors are thiophosphates. In some embodiments, the autotaxin inhibitors are phosphatidic acids derivatives. In some embodiments, the autotaxin inhibitors are cyclic phosphatidic acid analogs. In some embodiments, the autotaxin inhibitors are tyrosine based.

Other autotaxin inhibitors contemplated for use include and are not limited to FTY720-P and 532826. Additional autotaxin inhibitors contemplated for use include and are not limited to, those described in G. G. Durgam et. al., Bioorg. Med. Chem. Lett. 2006, 16, 633-640; G. G. Durgam et al., J. Med. Chem. 2005, 48, 4919-4930; V. Gududuru et al., Bioorg. Med. Chem. Lett. 2006, 16, 451-456; D. Baker, et al., J. Biol. Chem. 2006, 281, 22786-22793; R. Gupte et al., Bioorg. Med. Chem. Lett. 2010, 20, 7525-7528; R. Tanaka et al., Bioorg.

Med. Chem. Lett. 2011, 21, 4180-4182; G. Jiang et al., ChemMedChem 2007, 2, 679-690; WO 2008/157361 (published Dec. 24, 2008); WO 2010/040080 (Published Apr. 8, 2010); L. A. van Meeteren et al., Cancer Lett. 2008, 266, 203-208 (Autotaxin inhibitor FTY720-P); G. Ferry et al., J. Pharmacol. Exp. Ther. 2008, 327, 809-819 (Autotaxin inhibitor S32826); J. E. East et al., Bioorg. Med. Chem. Lett. 2010, 20, 7132-7136; P. Cui et al., Bioorg. Med. Chem. 2008, 16, 2212-2225; P. Cui et al., Bioorg. Med. Chem. Lett. 2007, 17, 1634-1640; G. Jiang et al., Bioorg. Med. Chem. Lett. 2011, 21, 5098-5101; K. Kano et al., Curr. Med. Chem. 2008, 15, 2122-2131; L. A. van Meeteren et al., J. Biol. Chem. 2005, 280, 21155-21161; E. Gendaszewska-Darmach et al., Bioorg. Med. Chem. Lett. 2012, 22, 2698-2700; J. Gajewak et al., Org. Lett. 2008, 10, 1111-1114; WO 2012/100018 (published on Jul. 26, 2012); US 2012/0190650 (published on Jul. 26, 2012; U.S. patent application Ser. No. 13/353,392); U.S. Pat. No. 8,673,882 (issued on Mar. 18, 2014; U.S. patent application Ser. No. 13/353,392); US 2010/0136650 (published on Jun. 3, 2010; U.S. patent application Ser. No. 12/572,921); U.S. Pat. No. 8,022,239 (issued on Sep. 20, 2011; U.S. patent application Ser. No. 12/572,921); US 2010/0016258 (published on Jan. 21, 2010; U.S. patent application Ser. No. 12/351,550); U.S. Pat. No. 8,378,100 (issued on Feb. 19, 2013; U.S. patent application Ser. No. 12/351,550), US 2006/0270634 (published on Nov. 30, 2006; U.S. patent application Ser. No. 11/418,561); H. Zhang et al., Cancer Res 2009, 69, 5441-5449; and R. Gupte et al., ChemMedChem 2011, 6, 922-935; all of which are incorporated by reference for the disclosure of such compounds.

In some embodiments, the autotaxin inhibitors are metal chelators. In some embodiments, the autotaxin inhibitors include, but are not limited to, L-histidine, ethylenediaminetetraacetic acid (EDTA), and 1,10-phenanthroline.

In other embodiments, the autotaxin inhibitors include the compounds disclosed in E. Barbayianni et al., Expert Opin Ther Pat. 2013, 23 (9), 1123-1132; A. L. Parrill and D. L. Baker, Expert Opin Ther Pat. 2010, 20(12), 1619-1625; L. Federico et al., Curr Drug Targets 2008, 9(8), 698-708; and H. M. Albers and H. Ovaa, Chem. Rev. 2012, 112, 2593-2603; all of which are incorporated by reference for the disclosure of such compounds.

Other Forms:

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers to a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, Handbook of Pharmaceutical Salts: Properties, Selection and Use, Weinheim/Zurich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, 2H, $^{3}$H, $^{13}$C, $^{14}$C, $^{15}$N, $^{18}$O, $^{17}$O, $^{35}$S, $^{18}$F, $^{36}$Cl. In one aspect, isotopically-labeled compounds described herein, for example those into which radioactive isotopes such as $^{3}$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from inhibition or reduction of autotaxin activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-diabetic agents. In certain embodiments the pharmaceutical composition further comprises one or more agents used to treat cardiovascular disease. In some embodiments, the cardiovascular agent is selected from the group consisting of: an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, and a fibrate, and any combination thereof.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Kits and Articles of Manufacture

Described herein are kits for decreasing blood glucose levels in an individual with a metabolic disorder in need thereof comprising administering to said individual an autotaxin inhibitor.

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of ATX, or in which ATX is a mediator or contributor to the symptoms or cause.

The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising the ATX inhibitor is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever.

Example 1

(S)-3-(6-(4-fluorobenzyl)-1,3-dioxo-5,6,11,11a-tetrahydro-1H-imidazo [1',5':1,6]pyrido[3,4-b]indol-2(3H)-yl)propanoic acid (Compound A)

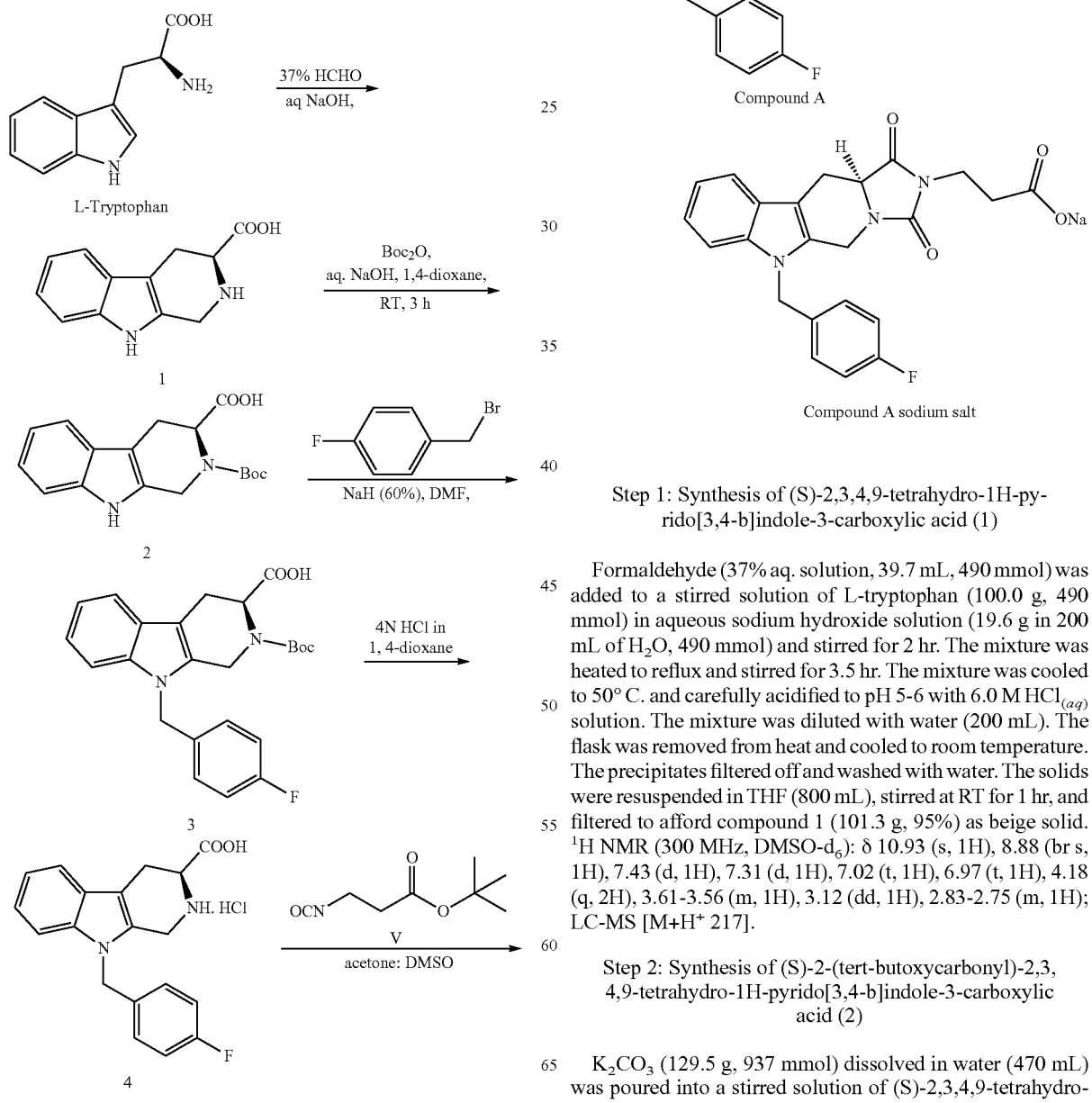

Step 1: Synthesis of (S)-2,3,4,9-tetrahydro-1H-pyrido[3,4-b]indole-3-carboxylic acid (1)

Formaldehyde (37% aq. solution, 39.7 mL, 490 mmol) was added to a stirred solution of L-tryptophan (100.0 g, 490 mmol) in aqueous sodium hydroxide solution (19.6 g in 200 mL of $H_2O$, 490 mmol) and stirred for 2 hr. The mixture was heated to reflux and stirred for 3.5 hr. The mixture was cooled to 50° C. and carefully acidified to pH 5-6 with 6.0 M $HCl_{(aq)}$ solution. The mixture was diluted with water (200 mL). The flask was removed from heat and cooled to room temperature. The precipitates filtered off and washed with water. The solids were resuspended in THF (800 mL), stirred at RT for 1 hr, and filtered to afford compound 1 (101.3 g, 95%) as beige solid. $^1$H NMR (300 MHz, DMSO-$d_6$): δ 10.93 (s, 1H), 8.88 (br s, 1H), 7.43 (d, 1H), 7.31 (d, 1H), 7.02 (t, 1H), 6.97 (t, 1H), 4.18 (q, 2H), 3.61-3.56 (m, 1H), 3.12 (dd, 1H), 2.83-2.75 (m, 1H); LC-MS [M+H$^+$ 217].

Step 2: Synthesis of (S)-2-(tert-butoxycarbonyl)-2,3,4,9-tetrahydro-1H-pyrido[3,4-b]indole-3-carboxylic acid (2)

$K_2CO_3$ (129.5 g, 937 mmol) dissolved in water (470 mL) was poured into a stirred solution of (S)-2,3,4,9-tetrahydro-1H-pyrido[3,4-b]indole-3-carboxylic acid (1; 101.3 g, 468 mmol) and di-tert-butyl dicarbonate (122.7 g, 562 mmol) in THF (470 mL) at 0° C. The reaction was stirred at room temperature overnight. The next day the THF was removed under reduced pressure and the remaining residue was carefully acidified to pH 3-4 with saturated citric acid solution. The precipitants filtered off and washed with water to afford compound 2 (143.5 g, 97%) as a beige powder. $^1$H NMR (300 MHz, DMSO-$d_6$): δ 12.75 (br s, 1H), 10.88 (s, ½H), 10.83 (s, ½H), 7.40 (d, 1H), 7.28-7.25 (m, 1H), 7.05 (t, 1H), 6.92 (t, 1H), 5.15-5.10 (m, 1H), 4.69 (t, 1H), 4.45-4.29 (m, 1H), 3.30-3.23 (m, 1H), 2.98-2.88 (m, 1H), 1.46 (s, 9×½H), 1.42 (s, 9×½H); LC-MS [M+H$^+$ 317].

Step 3: Synthesis of (S)-2-(tert-butoxycarbonyl)-9-(4-fluorobenzyl)-2,3,4,9-tetrahydro-1H-pyrido[3,4-b]indole-3-carboxylic acid (3)

The acid 2 (20.0 g, 63.2 mmol) in DMF (630 mL) was degassed and the flask was cooled in ice water bath. NaH (60% in mineral oil; 7.8 g, 196.0 mmol) was slowly added portionwise over 45 min at 0° C. and stirred for 1 hr. 4-fluorobenzyl bromide (8.7 mL, 69.5 mmol) was added dropwise over 45 min at 0° C. and stirred for 1.5 hr. The reaction quenched with water. The mixture diluted with water (1.8 L) and washed with EtOAc (1 L). The aqueous layer was acidified to pH 3-4 with solid citric acid. The mixture extracted with EtOAc (3×300 mL). The combined organic extracts were washed with water (900 mL), brine (200 mL), dried over Na$_2$SO$_4$, filtered, and concentrated under reduced pressure. The crude was purified by silica gel column chromatography using 0-30% EtOAc/Hexane to give a solid. The solid was washed with 10% CH$_2$Cl$_2$/hexane to afford the acid 3 (19.5 g, 72%) as a white powder. $^1$H NMR (300 MHz, DMSO-$d_6$): δ 12.81 (br s, 1H), 7.48-7.42 (m, 2H), 7.13-6.97 (m, 6H), 5.41-5.28 (m, 2H), 5.14-5.03 (m, 1H), 4.66-4.58 (m, 1H), 4.42-4.27 (m, 1H), 3.32-3.28 (m, 1H), 3.06-2.96 (m, 1H), 1.40 (s, 9×½H), 1.39 (s, 9×½H); LC-MS [M+H$^+$ 425].

Step 4: Synthesis of (S)-9-(4-fluorobenzyl)-2,3,4,9-tetrahydro-1H-pyrido[3,4-b]indole-3-carboxylic acid (4)

The acid 3 (18.9 g, 44.5 mmol), 4M HCl in 1,4-dioxane solution (56 mL, 222.7 mmol), and 1,4-dioxane (85 mL) stirred at RT overnight. The reaction diluted with water (200 mL) and neutralized to pH 7 with Et$_3$N. Water (400 mL) was added and the mixture stirred for 30 min. The solid was collected by filtration and washed with water (300 mL) to afford the amino acid 4 (13.0 g, 90%) as a pale yellow powder. $^1$H NMR (300 MHz, DMSO-$d_6$): δ 8.95 (br s, 1H), 7.48 (d, 1H), 7.39 (d, 1H), 7.14-6.99 (m, 6H), 5.33 (s, 2H), 4.24 (d, 1H), 4.08 (d, 1H), 3.63-3.58 (m, 1H), 3.17-3.10 (m, 1H), 2.86-2.81 (m, 1H); LC-MS [M+H$^+$ 325].

Step 5: Synthesis of tert-butyl 3-isocvanatopropionate (5)

β-Alanine tert-butyl ester hydrochloride (13.0, 71.6 mmol) in CH$_2$Cl$_2$ (240 mL) and saturated NaHCO$_{3(aq)}$ solution (240 mL) was degassed and the flask was cooled in ice water bath. Triphosgene (21.2 g, 71.6 mmol) was added in one portion under inert atmosphere at 0° C. The reaction stirred at 0° C. to RT over 2.5 hr. The reaction was diluted with water (500 mL) and poured into reparatory funnel. The layers separated and the aqueous layer was extracted with CH$_2$Cl$_2$. The combined organic extracts were washed with brine, dried over Na$_2$SO$_4$, filtered, and concentrated under reduced pressure to obtain crude tert-butyl 3-iso cyanatopropionate (11.5 g) as a yellow liquid. This crude material was directly used for next reaction without purification. $^1$H NMR (300 MHz, CDCl$_3$): δ 3.53 (t, 2H), 2.52 (t, 2H), 1.47 (s, 9H).

Step 6: Synthesis of tert-butyl (S)-3-(6-(4-fluorobenzyl)-1,3-dioxo-5,6,11,11a-tetrahydro-1H-imidazo[1',5':1,6]pyrido[3,4-b]indol-2(3H)-yl)propanoate (6)

The amino acid 5 (21.0 g, 64.7 mmol) and anhydrous DMA (260 mL) in 1 L round bottom flask equipped with condenser was degassed. tert-Butyl 3-isocyanatopropionate (V) (11.1 g, 64.7 mmol) was added and the mixture was heated to 100° C. overnight. The reaction cooled to room temperature and diluted with water (1.25 L) and brine (50 mL). The mixture extracted with EtOAc (3×300 mL). The combined organic extracts were washed with water (900 mL), brine (200 mL), dried over Na$_2$SO$_4$, filtered, and concentrated under reduced pressure. The crude material was purified through a silica gel column with 10% EtOAc/CH$_2$Cl$_2$. The fractions concentrated under reduce pressure to provide a solid. The solid was washed with 10% CH$_2$Cl$_2$/Hexane to afford the ester 6 (25.9 g, 84%). $^1$H NMR (300 MHz, DMSO-$d_6$): δ 7.54 (d, 1H), 7.47 (d, 1H), 7.16-7.02 (m, 6H), 5.42 (q, 2H), 4.88 (d, 1H), 4.41-4.30 (m, 2H), 3.62 (t, 2H), 3.31-3.23 (m, 1H), 2.77-2.68 (m, 1H), 1.34 (s, 9H); LC-MS [M+H$^+$ 478].

Step 7: Synthesis of (S)-3-(6-(4-fluorobenzyl)-1,3-dioxo-5,6,11,11a-tetrahydro-1H-imidazo [1',5':1,6]pyrido[3,4-b]indol-2(3H)-yl)propanoic acid (Compound A)

The tert-butyl ester 6 (20.0 g, 41.9 mmol) was added to a solution of 4N HCl in 1,4-dioxane (100 mL) at RT and stirred for 6 hr. The reaction was diluted with ice-cold water (1 L) and extracted with EtOAc (2×150 mL). The combined organic extracts were washed with Na$_2$SO$_4$, filtered, and concentrated under reduced pressure to obtain the crude. The crude was purified by silica gel column chromatography using 0-70% EtOAc/Hexane. The combined fractions were concentrated under reduced pressure to afford pale yellow foam (16.4 g). The foam was dissolved in isopropyl acetate (75 mL) and then ether (75 mL) was added. Pentane (10 mL) was added to the solution and sonicated until a precipitate formed. Pentane (100 mL) was added. The mixture stirred at RT for 1.5 hr. The solids filtered off and washed with isopropyl acetate: ether: pentane (150 mL, 1:1:1.5) to afford (S)-3-(6-(4-fluorobenzyl)-1,3-dioxo-5,6,11,11a-tetrahydro-1H-imidazo [1',5':1,6]pyrido[3,4-b]indol-2(3H)-yl)propanoic acid (Compound A) (12.8 g, 72%) as a white solid. $^1$H NMR (300 MHz, DMSO-$d_6$): δ 12.37 (s, 1H), 7.54 (d, 1H), 7.48 (d, 1H), 7.15-7.02 (m, 6H), 5.42 (q, 2H), 4.89 (d, 1H), 4.40-4.30 (m, 2H), 3.65 (d, 2H), 3.32-3.22 (m, 1H), 2.79-2.70 (m, 1H), 2.56-2.54 (m, 2H); LC-MS [M+H$^+$ 422].

Step 8: Synthesis of (S)-3-(6-(4-fluorobenzyl)-1,3-dioxo-5,6,11,11a-tetrahydro-1H-imidazo [1',5':1,6]pyrido[3,4-b]indol-2(3H)-yl)propanoic acid sodium salt (Compound A sodium salt)

(S)-3-(6-(4-fluorobenzyl)-1,3-dioxo-5,6,11,11a-tetrahydro-1H-imidazo[1',5':1,6]pyrido[3,4-b]indol-2(3H)-yl)propanoic acid (A) (40.35 g, 95.7 mmol) dissolved in tetrahydrofuran (960 mL) in 2 L round bottom flask equipped with addition funnel was degassed and cooled in ice water bath. 1M NaOH (86.2 mL, 86.2 mmol) was added dropwise over 3 hr at 0° C. The solvent removed under reduce pressure to afford (S)-3-(6-(4-fluorobenzyl)-1,3-dioxo-5,6,11,11a-tetrahydro-1H-imidazo[1',5':1,6]pyrido[3,4-b]indol-2(3H)-yl)propanoic acid sodium salt (Compound A sodium salt; 42.4 g, 100%) as a pale yellow solid. $^1$H NMR (300 MHz, DMSO-$d_6$): δ 7.53 (d, 1H), 7.47 (d, 1H), 7.16-7.02 (m, 6H), 5.40 (q, 2H), 4.89 (d, 1H), 4.36-4.28 (m, 2H), 3.56-3.49 (m, 2H), 3.27-3.20 (m, 1H), 2.76-2.67 (m, 1H), 2.17-2.11 (m, 2H); LC-MS [M+H$^+$ 422].

Example 2

Synthesis of 3-((6-Chloro-2-cyclopropyl-1-(1-ethyl-1H-pyrazol-4-yl)-7-fluoro-1H-indol-3-yl)thio)-2-fluorobenzoic acid (Compound B)

Route 1

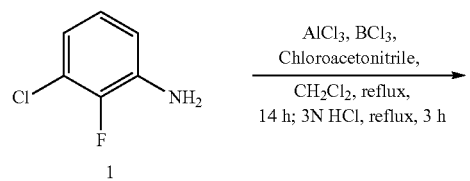

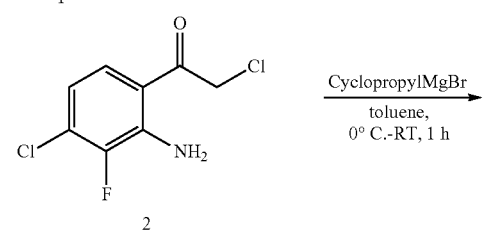

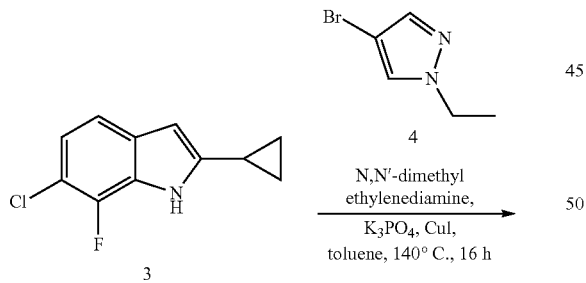

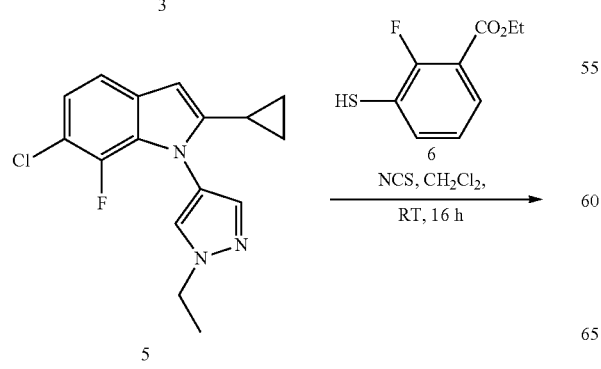

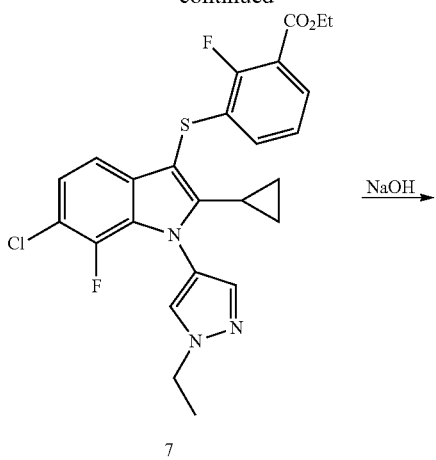

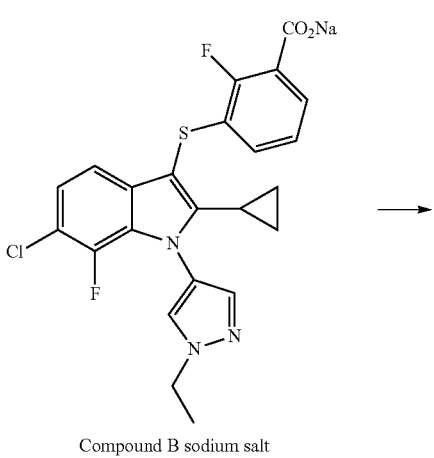

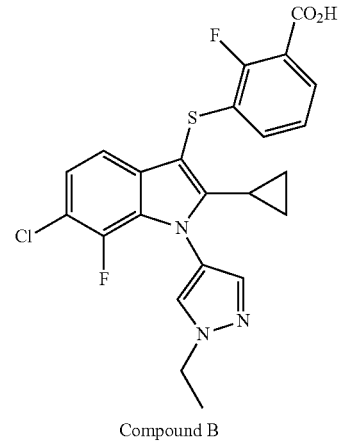

Compound B sodium salt

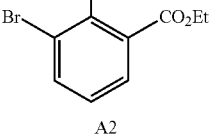

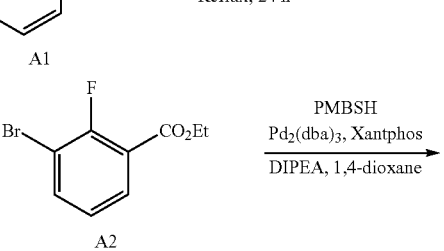

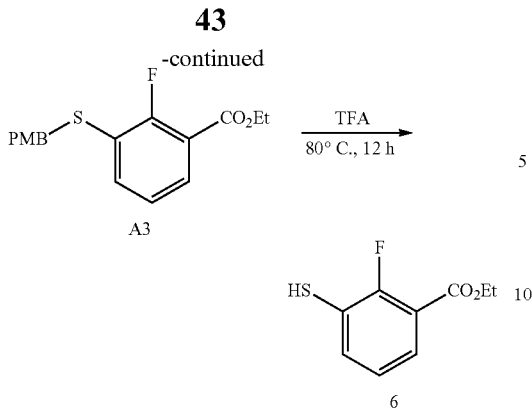

Step 1: Synthesis of 1-(2-amino-4-chloro-3-fluorophenyl)-2-chloroethan-1-one (2)

To a stirred solution of AlCl$_3$ (10.0 g, 75.01 mmol) and BCl$_3$ (1M in n-hexane) (74 mL, 75.01 mmol) in CH$_2$Cl$_2$ (80 mL) was added 3-chloro-2-fluoroaniline 1 (9.0 g, 6.18 mmol) followed by a solution of chloroacetonitrile (11.6 g, 153.64 mmol) in CH$_2$Cl$_2$ (20 mL) at 0° C. under inert atmosphere. The reaction mixture was allowed to stir at RT for 30 minutes; heated to reflux temperature and maintained for additional 14 h. The reaction mixture was then cooled to 0° C., added aqueous 3N HCl solution (100 mL) and raised the temperature to reflux and stirred for 3 h. After completion of the reaction by TLC, the reaction mixture was cooled RT, diluted with water (50 mL) and extracted with CH$_2$Cl$_2$ (2×150 mL). The combined organic extracts were dried over Na$_2$SO$_4$, filtered and concentrated under reduced pressure to obtain the crude. The crude was purified by triturating with n-pentane to afford compound 2 (4.5 g, 33%) as an off-white solid. $^1$H NMR (500 MHz, DMSO-d$_6$): δ 7.61 (d, J=9.0 Hz, 1H), 7.35 (br s, 2H), 6.72 (d, J=9.0 Hz, 1H), 5.06 (s, 2H).

Step 2: Synthesis of 6-chloro-2-cyclopropyl-7-fluoro-1H-indole (3)

To a stirred solution of compound 2 (4.5 g, 20.3 mmol) in toluene (50 mL) was added cyclopropyl magnesium bromide (0.5 M in THF; 102.0 mL, 50.9 mmol) at 0° C. under inert atmosphere. The reaction mixture was stirred at 0° C. for 15 min and then warmed to RT and stirring was continued for additional 1 h. After completion of the reaction by TLC, the reaction mixture was quenched with saturated ammonium chloride solution (10 mL) and extracted with EtOAc (3×75 mL). The combined organic extracts were dried over Na$_2$SO$_4$, filtered and concentrated under reduced pressure to obtain the crude. The crude was purified (silica gel chromatography; 1% EtOAc/Hexanes) to afford compound 3 (2.7 g, 63%) as an off-white solid. $^1$H NMR (500 MHz, DMSO-d$_6$): δ 11.55 (s, 1H), 7.18 (d, J=8.5 Hz, 1H), 6.97 (dd, J=8.5, 6.5 Hz, 1H), 6.16 (s, 1H), 2.03-1.99 (m, 1H), 0.99-0.96 (m, 2H), 0.83-0.80 (m, 2H); LC-MS (ESI): 91.6%; m/z 208.1 (M–H$^+$); (column: X Select CSH C-18, 50×3.0 mm, 3.5 μm); RT 4.32 min; 5 mM NH$_4$OAc: ACN; 0.8 mL/min).

Step 3: Synthesis of 4-bromo-1-ethyl-1H-pyrazole (4)

To a stirred solution of NaH (34.0 g, 0.85 mol; 60% in mineral oil) in THF (400 mL) was added a solution of 4-bromo-1H-pyrazole (50 g, 0.34 mol) in THF (100 mL) at 0° C. under inert atmosphere. The reaction mixture was warmed to RT and maintained at same temperature for 1 h. The reaction mixture was cooled again to 0° C. and added EtI (63.67 g, 0.408 mol) slowly for 5 min. The resultant solution was allowed to warm to RT and then stirred for 16 h. After completion of the reaction (monitored by TLC), the reaction mixture was quenched with ice-cold water (100 mL) and extracted with EtOAc (3×250 mL). The combined organic extracts were dried over Na$_2$SO$_4$, filtered and concentrated under reduced pressure to obtain the crude. The crude was purified (silica gel chromatography; 4-6% EtOAc/Hexanes) to afford compound 4 (43 g, 72%) as a pale yellow liquid. $^1$H NMR (500 MHz, CDCl$_3$): δ 7.45 (s, 1H), 7.41 (s, 1H), 4.15 (q, J=7.5 Hz, 2H), 1.47 (t, J=7.5 Hz, 3H); MS (ESI): m/z 175.0 (M+H$^+$).

Step 4: Synthesis of 6-chloro-2-cyclopropyl-1-(1-ethyl-1H-pyrazol-4-yl)-7-fluoro-1H-indole (5)

To a solution of compound 3 (4.3 g, 20.5 mmol) in toluene (50 mL) were added 4-bromo-1-ethyl-1H-pyrazole 4 (4.0 g, 22.8 mmol), potassium phosphate (11.0 g, 51.2 mmol), N,N'-dimethylethylenediamine (722 mg, 8.2 mmol) and Cu(I)I (390 mg, 2.0 mmol) at RT under inert atmosphere. The reaction solution was purged with argon for 15 min and then sealed the tube. The reaction mixture was heated to 140° C. and stirred for 16 h. After completion of the reaction by TLC, the reaction mixture was cooed to RT, diluted with EtOAc (50 mL) and filtered. The filtrate was washed with water (40 mL), brine (40 mL), dried over Na$_2$SO$_4$, filtered and concentrated under reduced pressure to obtain the crude. The crude was purified (silica gel chromatography; 9% EtOAc/Hexanes) to afford compound 5 (3.9 g, 63%) as a pale brown solid. $^1$H NMR (400 MHz, CDCl$_3$): δ 7.64 (s, 1H), 7.60 (s, 1H), 7.16 (d, J=8.4 Hz, 1H), 7.01 (dd, J=8.4, 6.4 Hz, 1H), 6.12 (s, 1H), 4.25 (q, J=7.2 Hz, 2H), 1.69-1.62 (m, 1H), 1.56 (t, J=7.2 Hz, 3H), 0.92-0.87 (m, 2H), 0.76-0.72 (m, 2H); LC-MS (ESI): 98.6%; m/z 304.3 (M+H$^+$); (column: X Select C-18, 50×3.0 mm, 3.5 μm); RT 4.23 min; 5 mM NH$_4$OAc: ACN; 0.8 mL/min).

Step 5: Synthesis of ethyl 3-bromo-2-fluorobenzoate (A2)

To a stirred solution of 3-bromo-2-fluorobenzoic acid A1 (25.0 g, 114.15 mmol) in ethanol (400 mL) was added conc. H$_2$SO$_4$ (3 mL) at RT and stirred at reflux temperature for 24 h. The reaction was monitored by LC-MS; after completion of the reaction, the reaction mixture was concentrated to obtain the residue. The residue was diluted with EtOAc (500 mL), washed with water (300 mL), brine (300 mL), dried over Na$_2$SO$_4$, filtered and concentrated under reduced pressure to afford compound A2 (26.0 g, 92%) as a light yellow liquid. $^1$H NMR (400 MHz, CDCl$_3$): δ 7.88-7.84 (m, 1H), 7.72-7.69 (m, 1H), 7.08-7.04 (m, 1H), 4.39 (q, J=7.2 Hz, 2H), 1.39 (t, J=7.2 Hz, 3H).

Step 6: Synthesis of ethyl 2-fluoro-3-((4-methoxybenzyl)thio)benzoate (A3)

1,4-dioxane (250 mL) was degassed by purging with N$_2$ gas for 30 min and to this, were added a solution of compound A2 (13.2 g, 53.4 mmol) in 1,4-dioxane (50 mL; degassed), (4-methoxyphenyl)methanethiol (PMBSH) (8.2 g, 53.4 mmol), xantphos (1.54 g, 2.66 mmol), diisopropyl ethyl amine (19.6 mL, 106.8 mmol) and Pd$_2$(dba)$_3$ (1.22 g, 1.33 mmol) at RT. The reaction mixture was heated to 90° C. and stirred for 2 h. The reaction was monitored by TLC; after completion of the reaction, the reaction mixture was diluted with hexane (450 mL) and stirred at RT for 15 min. The resultant solution was filtered through celite and washed with hexane (100 mL). The filtrate was washed water (250 mL) dried over Na$_2$SO$_4$, filtered and concentrated under reduced pressure to obtain the crude. The crude was purified through silica gel column chromatography using 3-4% EtOAc/Hexanes to afford compound A3 (15 g, 88%) as pale yellow solid. $^1$H NMR (500 MHz, CDCl$_3$): δ 7.78-7.74 (m, 1H), 7.43-7.39 (m, 1H), 7.19 (d, J=8.0 Hz, 2H), 7.07-7.04 (m, 1H), 6.80 (d, J=8.0 Hz, 2H), 4.41 (q, J=7.2 Hz, 2H), 4.08 (s, 2H), 3.78 (s, 3H), 1.41 (t, J=7.2 Hz, 3H). LC-MS (ESI): 89.7%; m/z 318.9 (M−H$^+$); (column: X Select CSH C-18, 50×3.0 mm, 3.5 μm); RT 4.22 min; 5 mM NH$_4$OAc: ACN; 0.8 mL/min).

Step 7: Synthesis of ethyl 2-fluoro-3-mercaptobenzoate (6)

A stirred solution of compound A3 (30.0 g, 93.75 mmol) in TFA (54.5 mL) was heated to 80° C. and stirred for 12 h under inert atmosphere. The reaction was monitored by TLC; after completion of the reaction, the volatiles were removed under reduced pressure. The residue was dissolved in ice-cold water (100 mL), basified with solid sodium bicarbonate and extracted with EtOAc (2×200 mL). The combined organic extracts were dried over Na$_2$SO$_4$, filtered and concentrated under reduced pressure to obtain the crude. The crude was purified through silica gel column chromatography using 3% EtOAc/Hexanes to afford compound 6 (11.7 g, 62%) as a pale brown syrup. $^1$H NMR (500 MHz, CDCl$_3$): δ 7.70-7.66 (m, 1H), 7.48-7.44 (m, 1H), 7.08-7.04 (m, 1H), 4.20 (q, J=7.5 Hz, 2H), 3.67 (s, 1H), 1.40 (t, J=7.5 Hz, 3H); LC-MS (ESI): 91.8%; m/z 199.0 (M−H$^+$); (column: X Select CSH C-18, 50×3.0 mm, 3.5 μm); RT 2.60 min; 5 mM NH$_4$OAc: ACN; 0.8 mL/min).

Step 8: Synthesis of ethyl 3-((6-chloro-2-cyclopropyl-1-(1-ethyl-1H-pyrazol-4-yl)-7-fluoro-1H-indol-3-yl)thio)-2-fluorobenzoate (7)

To a stirred solution of ethyl 2-fluoro-3-mercaptobenzoate 6 (2.8 g, 14.0 mmol) in CH$_2$Cl$_2$ (30 mL) under inert atmosphere was added NCS (1.9 g, 14.0 mmol) at RT and allowed to stir for 2 h. To this, compound 5 (3.9 g, 12.8 mmol) in CH$_2$Cl$_2$ (10 mL) was added at RT and stirred for 16 h. After completion of the reaction by TLC, the reaction mixture was diluted with water (100 mL) and extracted with CH$_2$Cl$_2$ (2×80 mL). The combined organic extracts were washed with water (2×200 mL), dried over Na$_2$SO$_4$, filtered and concentrated under reduced pressure to obtain the crude. The crude was purified by triturating with n-pentane (2×50 mL) to afford 7 (5.2 g, 81%) as a pale yellow solid. $^1$H NMR (400 MHz, CDCl$_3$): δ 7.66-7.7.60 (m, 3H), 7.18 (d, J=8.4 Hz, 1H), 7.08 (dd, J=8.4, 6.5 Hz, 1H), 6.93 (t, J=8.4 Hz, 1H), 6.79-6.75 (m, 1H), 4.40 (q, J=7.2 Hz, 2H), 4.26 (q, J=7.6 Hz, 2H), 1.74-1.68 (m, 1H), 1.56 (t, J=7.2 Hz, 3H), 1.41 (t, J=7.6 Hz, 3H), 1.08-1.04 (m, 2H), 0.89-0.84 (m, 2H); MS (ESI): m/z 502.5 (M+H$^+$); HPLC: 97.5%; (column: Acquity BEH C-18 (50× 2.1 mm, 1.7μ); RT 3.44 min; ACN: 0.025% TFA (aq); 0.5 mL/min.

Step 9: Synthesis of 3-(6-chloro-2-cyclopropyl-1-(1-ethyl-1H-pyrazol-4-yl)-7-fluoro-1H-indol-3-yl)thio)-2-fluorobenzoic acid sodium salt (8)

1.0 M NaOH (10.25 mL, 10.2 mmol) was added to a solution of compound 7 (5.14 g, 10.2 mmol) in THF/MeOH (3:1)(56 mL). The mixture was heated at 65° C. for 1.5 h. Additional 1.0 M NaOH (0.23 mL, 0.2 mmol) was added to the reaction and heated at 65° C. for 0.5 h. The mixture was concentrated under reduced pressure to afford the crude acid sodium salt (5.12 g, 100%) as a pale pink solid. The crude solid (600 mg) in THF/EtOH (4:1) (6 mL) and a few drops of water. The mixture filtered and concentrated under reduced pressure and precipitants formed. The solids filtered off and washed with THF/EtOH (9:1) to afford 3-((6-chloro-2-cyclopropyl-1-(1-ethyl-1H-pyrazol-4-yl)-7-fluoro-1H-indol-3-yl)thio)-2-fluorobenzoic acid sodium salt (Compound B sodium salt; 449 mg) as an off white solid. $^1$H NMR (300 MHz, DMSO-d$_6$): δ 8.26 (s, 1H), 7.79 (m, 1H), 7.18-7.13 (m, 3H), 6.81 (t, 1H), 6.43-6.38 (m, 1H), 4.21 (q, 2H), 1.84-1.72 (m, 1H), 1.42 (t, 3H), 0.96-0.93 (m, 2H), 0.84-0.80 (m, 2H); LC-MS: 474 (M$^+$)

3-((6-Chloro-2-cyclopropyl-1-(1-ethyl-1H-pyrazol-4-yl)-7-fluoro-1H-indol-3-yl)thio)-2-fluorobenzoic acid (Compound B)

To compound B sodium salt (50 mg, 0.10 mmol) suspended in CH$_2$Cl$_2$ (1 mL) and water (1 mL) was added sat. citric acid until pH 3. The suspension stirred until clear solution. The organic layer was separated, washed with brine, dried over Na$_2$SO$_4$, filtered, and concentrated under reduced pressure to obtain the crude material to afford compound B as a white solid (33 mg, 70%) $^1$H NMR (300 MHz, DMSO-d$_6$): δ 13.39 (s, 1H), 8.24 (s, 1H), 7.79 (s, 1H), 7.57 (t, 1H), 7.22-7.06 (m, 3H), 6.80 (t, 1H), 4.21 (q, 2H), 1.84-1.72 (m, 1H), 1.42 (t, 3H), 0.96-0.88 (m, 2H), 0.86-0.80 (m, 2H); LC-MS: 474 (M$^+$)

Alternative Route to Intermediate 7:

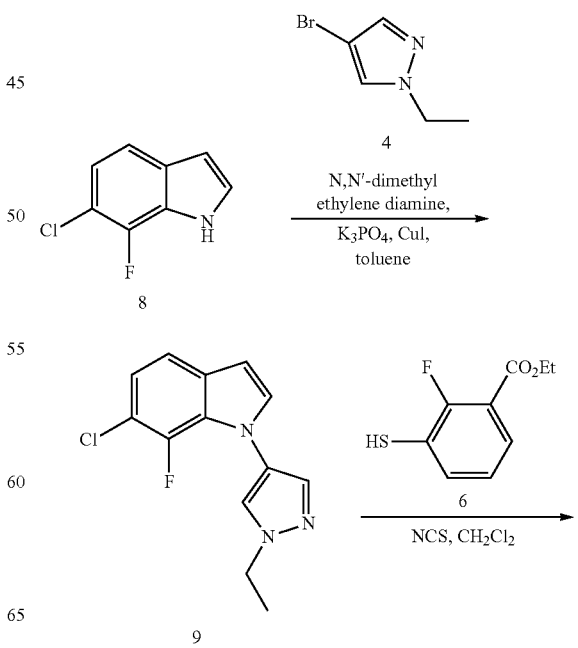

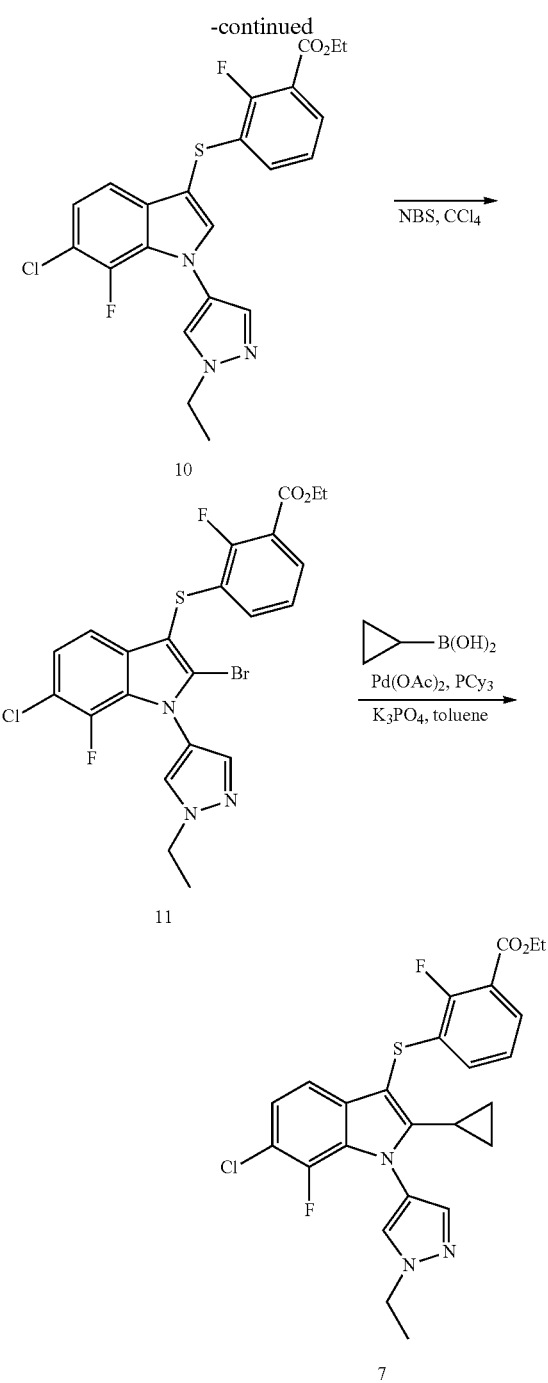

Step 1: Synthesis of 6-chloro-1-(1-ethyl-1H-pyrazol-4-yl)-7-fluoro-1H-indole (9)

To a stirred solution of 6-chloro-7-fluoro-1H-indole 8 (400 mg, 2.36 mmol) in toluene (10 mL) were added 4-bromo-1-ethyl-1H-pyrazole 4 (Step 3 above; 414 mg, 2.36 mmol), potassium phosphate (1.25 g, 5.91 mmol), N,N'-dimethylethylenediamine (84 mg, 0.95 mmol) and Cu(I)I (45 mg, 0.24 mmol) at RT under inert atmosphere. The resulted solution was purged with argon and sealed the tube. The reaction mixture was then heated to 140° C. for 16 h. After completion of the reaction (monitored by TLC), the reaction mixture was cooled to RT, diluted with hexane (10 mL) and filtered through a short pad of celite. The filtrate was washed with water (2×10 mL), dried over $Na_2SO_4$, filtered and concentrated under reduced pressure to obtain the crude. The crude was purified (silica gel chromatography; 8-10% EtOAc/Hexanes) to afford compound 9 (224 mg, 36%) as a light brown thick liquid. $^1$H NMR (500 MHz, $CDCl_3$): δ 7.64 (s, 1H), 7.61 (s, 1H), 7.31 (d, J=8.0 Hz, 1H), 7.12-7.07 (m, 2H), 6.60-6.59 (m, 1H), 4.22 (q, J=7.5 Hz, 2H), 1.55 (t, J=7.5 Hz, 3H); LC-MS (ESI): 94.7%; m/z 264.1 (M+H$^+$); (column: X Select C-18, 50×3.0 mm, 3.5 μm); RT 3.87 min; 5 mM $NH_4OAc$: ACN; 0.8 mL/min).

Step 2: Synthesis of ethyl 3-((6-chloro-1-(1-ethyl-1H-pyrazol-4-yl)-7-fluoro-1H-indol-3-yl)thio)-2-fluorobenzoate (10)

To a stirred solution of ethyl 2-fluoro-3-mercaptobenzoate 6 (Step 7 above; 212 mg, 1.06 mmol) in $CH_2Cl_2$ (4 mL) under inert atmosphere was added NCS (156 mg, 1.16 mmol) at 0° C. and allowed to stir at RT for 1 h. The reaction mixture was cooled to 0° C. and compound 3 (280 mg, 1.06 mmol) in $CH_2Cl_2$ (1 mL) was added slowly and stirred at RT for 16 h. After completion of the reaction by TLC, the reaction mixture was diluted with $CH_2Cl_2$ (15 mL) and washed with water (2×20 mL), dried over $Na_2SO_4$, filtered and concentrated under reduced pressure to obtain the crude. The crude was purified (silica gel chromatography; 8-10% EtOAc/Hexanes) to afford compound 10 (300 mg, 61%) as a pale brown solid. $^1$H NMR (500 MHz, $CDCl_3$): δ 7.69-7.64 (m, 3H), 7.44 (s, 1H), 7.27 (t, J=8.0 Hz, 1H), 7.16 (dd, J=8.5, 6.0 Hz, 1H), 7.01-6.94 (m, 2H), 4.39 (q, J=7.5 Hz, 2H), 4.24 (q, J=7.0 Hz, 2H), 1.57 (t, J=7.0 Hz, 3H), 1.40 (t, J=7.5 Hz, 3H); LC-MS (ESI): 98.6%; m/z 462.3 (M+H$^+$); (column: X Select C-18, 50×3.0 mm, 3.5 μm); RT 4.70 min; 5 mM $NH_4OAc$: ACN; 0.8 mL/min).

Step 3: Synthesis of ethyl 3-((2-bromo-6-chloro-1-(1-ethyl-1H-pyrazol-4-yl)-7-fluoro-1H-indol-3-yl)thio)-2-fluorobenzoate (11)

To a stirred solution of compound 10 (200 mg, 0.43 mmol) in $CCl_4$ (10 mL) under inert atmosphere was added NBS (178 mg, 0.99 mmol) at RT and stirred for 16 h. After completion of the reaction by TLC, the reaction mixture was diluted with water (10 mL) and extracted with $CH_2Cl_2$ (2×20 mL). The combined organic extracts were washed with brine (10 mL), dried over $Na_2SO_4$, filtered and concentrated under reduced pressure to obtain the crude. The crude was purified (silica gel chromatography; 5-7% EtOAc/Hexanes) to afford compound 11 (180 mg, 77%) as an off-white solid. $^1$H NMR (500 MHz, $CDCl_3$): δ 7.70-7.67 (m, 1H), 7.65 (s, 2H), 7.30 (d, J=8.0 Hz, 1H), 7.17 (dd, J=8.5, 6.0 Hz, 1H), 7.00-6.98 (m, 2H), 4.40 (q, J=7.5 Hz, 2H), 4.27 (q, J=7.5 Hz, 2H), 1.58 (t, J=7.5 Hz, 3H), 1.40 (t, J=7.5 Hz, 3H); LC-MS (ESI): 99.5%; m/z 542.4 (M$^+$+2); (column: X Select CSH C-18, 50×3.0 mm, 3.5 μm); RT 4.80 min; 5 mM $NH_4OAc$: ACN; 0.8 mL/min).

Step 4: Synthesis of ethyl 3-((6-chloro-2-cyclopropyl-1-(1-ethyl-1H-pyrazol-4-yl)-7-fluoro-1H-indol-3-yl)thio)-2-fluorobenzoate (7)

A solution of compound 11 (150 mg, 0.27 mmol) in toluene (10 mL) under inert atmosphere was purged with argon at RT for 10 min. To this, cyclopropylboronic acid (48 mg, 0.55 mmol), tricyclohexyl phosphine (16 mg, 0.05 mmol), Pd(OAc)$_2$ (6 mg, 0.02 mmol) and potassium phosphate (202 mg, 0.01 mmol) were added at RT under argon. The resultant solution was purged again with argon at RT for 5 min. The reaction mixture was then heated to reflux temperature and stirred for 3 h. The reaction was monitored by TLC & LC-MS; after completion of the reaction, the reaction was cooled to RT, diluted with EtOAc (20 mL) and filtered. The filtrate was washed with water (2×10 mL) and brine (10 mL), dried over Na$_2$SO$_4$, filtered and concentrated under reduced pressure to obtain the crude. This was purified (silica gel chromatography; 6% EtOAc/Hexanes) to afford 7 as a pale yellow solid. $^1$H NMR (400 MHz, CDCl$_3$): δ 7.66-7.7.60 (m, 3H), 7.18 (d, J=8.4 Hz, 1H), 7.08 (dd, J=8.4, 6.5 Hz, 1H), 6.93 (t, J=8.4 Hz, 1H), 6.79-6.75 (m, 1H), 4.40 (q, J=7.2 Hz, 2H), 4.26 (q, J=7.6 Hz, 2H), 1.74-1.68 (m, 1H), 1.56 (t, J=7.2 Hz, 3H), 1.41 (t, J=7.6 Hz, 3H), 1.08-1.04 (m, 2H), 0.89-0.84 (m, 2H); LC-MS (ESI): 92.9%; m/z 502.5 (M$^+$); (column: X Select CSH C-18, 50×3.0 mm, 3.5 µm); RT 4.85 min; 5 mM NH$_4$OAc: ACN; 0.8 mL/min); HPLC: 93.1%; (column: Acquity BEH C-18 (50×2.1 mm, 1.7µ); RT 3.44 min; ACN: 0.025% TFA (aq); 0.5 mL/min.

Example 3

Synthesis of 3-((2,6-dichloro-7-fluoro-1-(1-propyl-1H-pyrazol-4-yl)-1H-indol-3-yl)thio)-2-fluorobenzoic acid (Compound C)

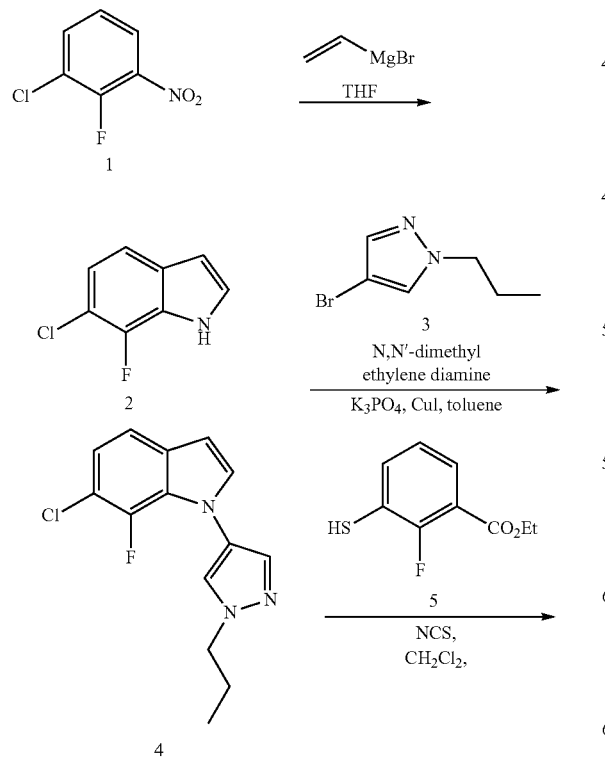

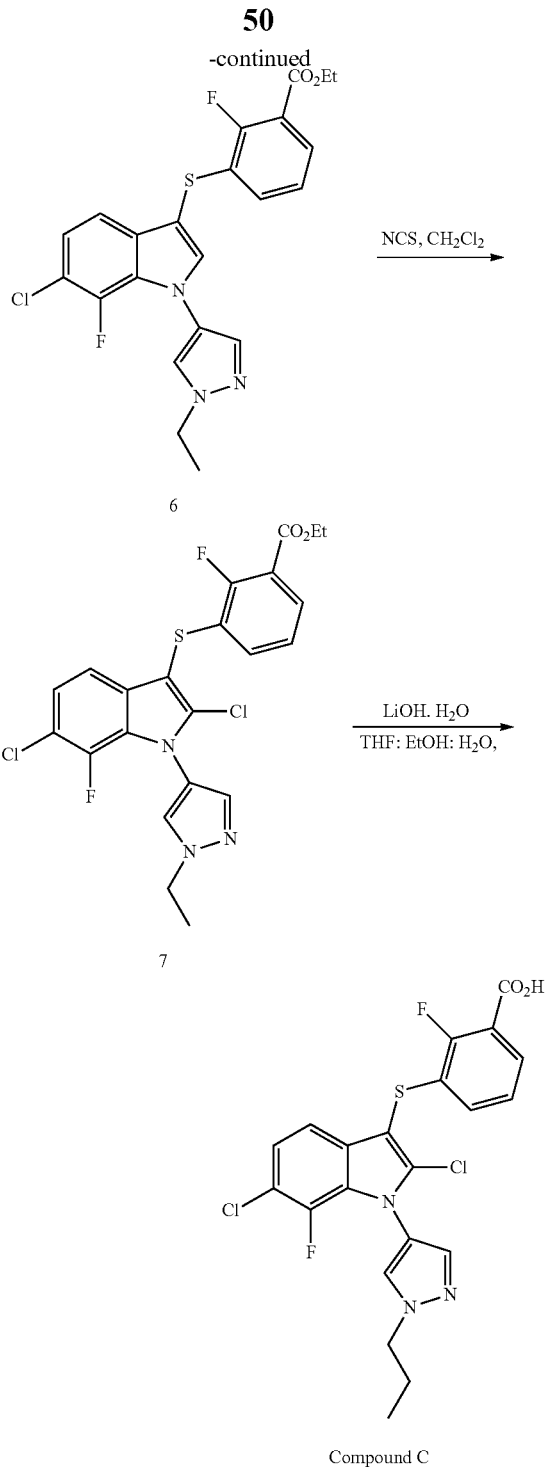

Compound C

Step 1: Synthesis of 6-chloro-7-fluoro-1H-indole (2)

To a stirred solution of 1-chloro-2-fluoro-3-nitrobenzene 1 (10.0 g, 56.98 mmol) in THF (100 mL) under inert atmosphere was added vinyl magnesium bromide (1M in THF solution; 170 mL, 170.94 mmol) at RT, cooled to −40° C. and stirred for 30 min. The reaction was monitored by TLC; after completion of the reaction, the reaction mixture was quenched with saturated NH$_4$Cl solution (50 mL), extracted with EtOAc (2×50 mL). The combined organic extracts were washed with NH$_4$Cl solution (40 mL), dried over Na$_2$SO$_4$, filtered and concentrated under reduced pressure to obtain the crude. This was purified by silica gel column chromatography using 2% EtOAc/Hexanes to afford compound 2 (1.1 g, 11.4%) as a brown oil. $^1$H NMR (500 MHz, CDCl$_3$): δ 8.36 (br s, 1H), 7.31 (d, J=8.0 Hz, 1H), 7.25-7.22 (m, 1H), 7.08-7.05 (m, 1H), 6.56-6.54 (m, 1H).

Step 2: Synthesis of 6-chloro-7-fluoro-1-(1-propyl-1H-pyrazol-4-yl)-1H-indole (3)

To a stirred solution of compound 2 (1.1 g, 6.48 mmol) in toluene (15 mL) under inert atmosphere were added N,N'-dimethyl ethylene diamine (229 mg, 2.60 mmol), potassium phosphate (3.44 g, 16.27 mmol), 4-bromo-1-propyl-1H-pyrazole 3 (Example 2, Step 3; 1.21 g, 6.50 mmol), CuI (124 mg, 0.65 mmol) at RT, degassed under argon for 15 min; heated to 140° C. and stirred for 20 h in sealed tube. The reaction was monitored by TLC; after completion of the reaction, the reaction mixture was diluted with EtOAc (30 mL), filtered and the filtrate was concentrated under reduced pressure to obtain the crude. This was purified by silica gel column chromatography using 8-10% EtOAc/Hexanes to afford compound 4 (1.3 g, 72%) as brown liquid. $^1$H NMR (500 MHz, CDCl$_3$): δ 7.64 (s, 1H), 7.60 (s, 1H), 7.31 (d, J=7.5 Hz, 1H), 7.12-7.07 (m, 2H), 6.60 (s, 1H), 4.13 (t, J=7.0 Hz, 2H), 1.99-1.91 (m, 2H), 0.97 (t, J=8.0 Hz, 3H); LC-MS (ESI): 93.5%; m/z 278.2 (M+H$^+$); (column: X Select CSH C-18, 50×3.0 mm, 3.5 μm); RT 4.08 min; 5 mM NH$_4$OAc: ACN; 0.8 mL/min).

Step 3: Synthesis of ethyl 3-((6-chloro-7-fluoro-1-(1-propyl-1H-pyrazol-4-yl)-1H-indol-3-yl)thio)-2-fluorobenzoate (6)

To a stirred solution of ethyl 2-fluoro-3-mercaptobenzoate (5; 108 mg, 0.54 mmol) in CH$_2$Cl$_2$ (3 mL) under inert atmosphere was added NCS (72 mg, 0.54 mmol) at RT and stirred for 1 h. To this, compound 4 (150 mg, 0.54 mmol) was added and stirred for 16 h. The reaction was monitored by TLC; after completion of the reaction, the reaction mixture was diluted with water (25 mL) and extracted with CH$_2$Cl$_2$ (2×25 mL). The combined organic extracts were washed with brine (20 mL), dried over Na$_2$SO$_4$, filtered and concentrated under reduced pressure to obtain the crude. This was purified by silica gel column chromatography using 10% EtOAc/Hexanes to afford compound 6 (130 mg, 50%) as an off-white solid. $^1$H NMR (500 MHz, CDCl$_3$): δ 7.69 (s, 1H), 7.67-7.64 (m, 2H), 7.44 (s, 1H), 7.29-7.27 (m, 1H), 7.17-7.14 (m, 1H), 7.01-6.94 (m, 2H), 4.40 (q, J=7.5 Hz, 2H), 4.15 (t, J=8.0 Hz, 2H), 1.98-1.94 (m, 2H), 1.40 (t, J=7.5 Hz, 3H), 0.98 (t, J=8.0 Hz, 3H); LC-MS (ESI): 97.6%; m/z 476.7 (M+H$^+$); (column: X Select CSH C-18, 50×3.0 mm, 3.5 μm); RT 4.84 min; 5 mM NH$_4$OAc: ACN; 0.8 mL/min).

Step 4: Synthesis of ethyl 3-((2,6-dichloro-7-fluoro-1-(1-propyl-1H-pyrazol-4-yl)-1H-indol-3-yl)thio)-2-fluorobenzoate (7)

To a stirred solution of ethyl 3-((6-chloro-7-fluoro-1-(1-propyl-1H-pyrazol-4-yl)-1H-indol-3-yl)thio)-2-fluorobenzoate 6 (100 mg, 0.21 mmol) in CH$_2$Cl$_2$ (3 mL) was added NCS (33.7 mg, 0.25 mmol) at RT under inert atmosphere. After 8 h stirring, additional NCS (33.7 mg, 0.25 mmol) was added at RT and stirred again for 24 h. The reaction was monitored by TLC; after completion of the reaction, the reaction mixture was diluted with water (20 mL) and extracted with CH$_2$Cl$_2$ (2×20 mL). The combined organic extracts were washed with brine (15 mL), dried over Na$_2$SO$_4$, filtered and concentrated under reduced pressure to obtain the crude. This was purified by silica gel column chromatography using 9-11% EtOAc/Hexanes to afford compound 7 (50 mg, 47%) as an off-white solid. $^1$H NMR (400 MHz, CDCl$_3$): δ 7.71-7.67 (m, 1H), 7.66 (s, 1H), 7.64 (s, 1H), 7.30 (d, J=8.8 Hz, 1H), 7.18 (dd, J=8.4, 6.0 Hz, 1H), 7.04-6.97 (m, 2H), 4.40 (q, J=7.2 Hz, 2H), 4.18 (t, J=7.2 Hz, 2H), 2.04-1.93 (m, 2H), 1.40 (t, J=7.2 Hz, 3H), 0.97 (t, J=7.2 Hz, 3H); LC-MS (ESI): 98.8%; m/z 510.4 (M+H$^+$); (column: X Select CSH C-18, 50×3.0 mm, 3.5 μm); RT 4.94 min; 5 mM NH$_4$OAc: ACN; 0.8 mL/min).

Step 5: Synthesis of 3-(2,6-dichloro-7-fluoro-1-(1-propyl-1H-pyrazol-4-yl)-1H-indol-3-yl)thio)-2-fluorobenzoic acid (Compound C)

To a stirred solution of compound 7 (50 mg, 0.09 mmol) in THF:EtOH:H$_2$O (3:1:1, 5 mL) under inert atmosphere was added LiOH.H$_2$O (12.3 mg, 0.29 mmol) at RT and stirred for 5 h. The reaction was monitored by TLC; after completion of the reaction, the volatiles were removed under reduced pressure. The residue was diluted with water (10 mL), acidified with 1N HCl and extracted with CH$_2$Cl$_2$ (2×10 mL). The combined organic extracts were washed with brine (10 mL), dried over Na$_2$SO$_4$, filtered and concentrated under reduced pressure to obtain the crude. This was triturated with n-pentane (2×5 mL) to afford the title compound C (15 mg, 34%) as an off-white solid. $^1$H NMR (400 MHz, DMSO-d$_6$): δ 13.24 (br s, 1H), 8.29 (s, 1H), 7.83 (s, 1H), 7.64-7.60 (m, 1H), 7.36-7.34 (m, 2H), 7.15-7.05 (m, 2H), 4.16 (t, J=7.2 Hz, 2H), 1.89-1.80 (m, 2H), 0.85 (t, J=7.2 Hz, 3H); MS (ESI): 480.1 (M−H$^+$); HPLC: 97.0%; (column: Acquity BEH C-18 (50× 2.1 mm, 1.7μ); RT 2.86 min; ACN: 0.025% TFA (aq); 0.5 mL/min.

Example 4

Synthesis of 6-((6-chloro-2-cyclopropyl-1-(1-ethyl-1H-pyrazol-4-yl)-7-fluoro-1H-indol-3-yl)thio)picolinic acid sodium salt (Compound D sodium salt)

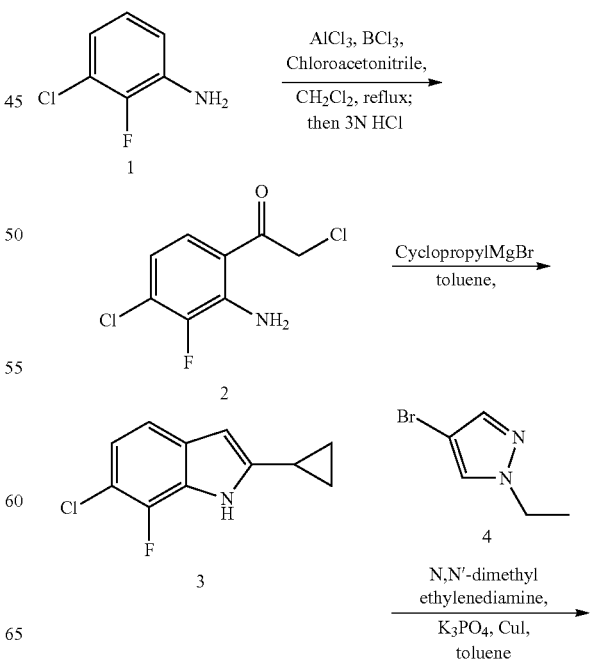

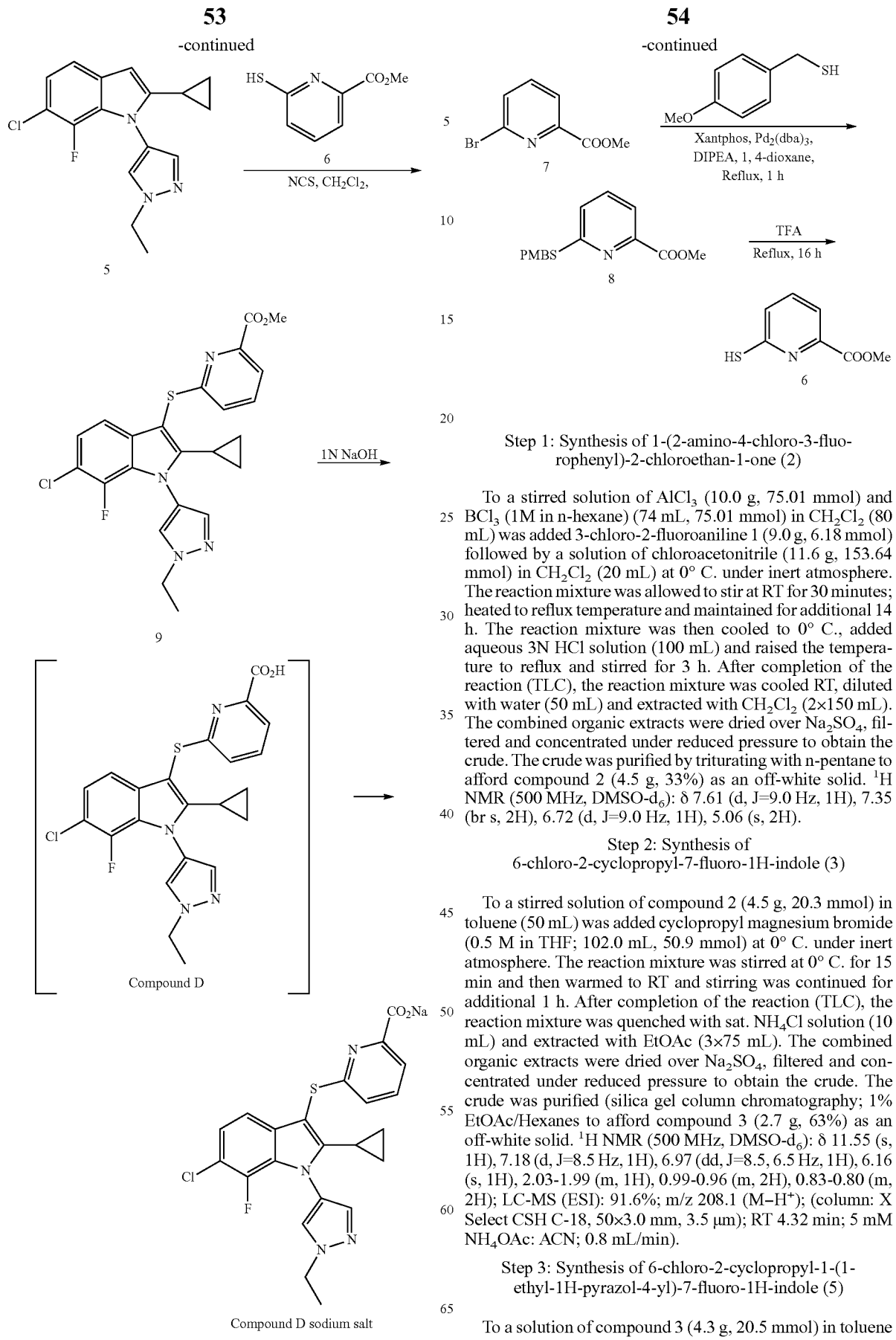

Step 1: Synthesis of 1-(2-amino-4-chloro-3-fluorophenyl)-2-chloroethan-1-one (2)

To a stirred solution of AlCl$_3$ (10.0 g, 75.01 mmol) and BCl$_3$ (1M in n-hexane) (74 mL, 75.01 mmol) in CH$_2$Cl$_2$ (80 mL) was added 3-chloro-2-fluoroaniline 1 (9.0 g, 6.18 mmol) followed by a solution of chloroacetonitrile (11.6 g, 153.64 mmol) in CH$_2$Cl$_2$ (20 mL) at 0° C. under inert atmosphere. The reaction mixture was allowed to stir at RT for 30 minutes; heated to reflux temperature and maintained for additional 14 h. The reaction mixture was then cooled to 0° C., added aqueous 3N HCl solution (100 mL) and raised the temperature to reflux and stirred for 3 h. After completion of the reaction (TLC), the reaction mixture was cooled RT, diluted with water (50 mL) and extracted with CH$_2$Cl$_2$ (2×150 mL). The combined organic extracts were dried over Na$_2$SO$_4$, filtered and concentrated under reduced pressure to obtain the crude. The crude was purified by triturating with n-pentane to afford compound 2 (4.5 g, 33%) as an off-white solid. $^1$H NMR (500 MHz, DMSO-d$_6$): δ 7.61 (d, J=9.0 Hz, 1H), 7.35 (br s, 2H), 6.72 (d, J=9.0 Hz, 1H), 5.06 (s, 2H).

Step 2: Synthesis of 6-chloro-2-cyclopropyl-7-fluoro-1H-indole (3)

To a stirred solution of compound 2 (4.5 g, 20.3 mmol) in toluene (50 mL) was added cyclopropyl magnesium bromide (0.5 M in THF; 102.0 mL, 50.9 mmol) at 0° C. under inert atmosphere. The reaction mixture was stirred at 0° C. for 15 min and then warmed to RT and stirring was continued for additional 1 h. After completion of the reaction (TLC), the reaction mixture was quenched with sat. NH$_4$Cl solution (10 mL) and extracted with EtOAc (3×75 mL). The combined organic extracts were dried over Na$_2$SO$_4$, filtered and concentrated under reduced pressure to obtain the crude. The crude was purified (silica gel column chromatography; 1% EtOAc/Hexanes to afford compound 3 (2.7 g, 63%) as an off-white solid. $^1$H NMR (500 MHz, DMSO-d$_6$): δ 11.55 (s, 1H), 7.18 (d, J=8.5 Hz, 1H), 6.97 (dd, J=8.5, 6.5 Hz, 1H), 6.16 (s, 1H), 2.03-1.99 (m, 1H), 0.99-0.96 (m, 2H), 0.83-0.80 (m, 2H); LC-MS (ESI): 91.6%; m/z 208.1 (M−H$^+$); (column: X Select CSH C-18, 50×3.0 mm, 3.5 μm); RT 4.32 min; 5 mM NH$_4$OAc: ACN; 0.8 mL/min).

Step 3: Synthesis of 6-chloro-2-cyclopropyl-1-(1-ethyl-1H-pyrazol-4-yl)-7-fluoro-1H-indole (5)

To a solution of compound 3 (4.3 g, 20.5 mmol) in toluene (50 mL) were added 4-bromo-1-ethyl-1H-pyrazole 4 (Example 2, Step 3; 4.0 g, 22.8 mmol), potassium phosphate (11.0 g, 51.2 mmol), N,N'-dimethylethylenediamine (722 mg, 8.2 mmol) and Cu(I)I (390 mg, 2.0 mmol) at RT under inert atmosphere. The reaction solution was purged with argon for 15 min and then sealed the tube. The reaction mixture was heated to 140° C. and stirred for 16 h. After completion of the reaction (TLC), the reaction mixture was cooled to RT, diluted with EtOAc (50 mL) and filtered. The filtrate was washed with water (40 mL), brine (40 mL), dried over $Na_2SO_4$, filtered and concentrated under reduced pressure to obtain the crude. The crude was purified (silica gel column chromatography; 9% EtOAc/Hexanes) to afford compound 5 (3.9 g, 63%) as a pale brown solid. $^1H$ NMR (400 MHz, $CDCl_3$): δ 7.64 (s, 1H), 7.60 (s, 1H), 7.16 (d, J=8.4 Hz, 1H), 7.01 (dd, J=8.4, 6.4 Hz, 1H), 6.12 (s, 1H), 4.25 (q, J=7.2 Hz, 2H), 1.69-1.62 (m, 1H), 1.56 (t, J=7.2 Hz, 3H), 0.92-0.87 (m, 2H), 0.76-0.72 (m, 2H); LC-MS (ESI): 98.6%; m/z 304.3 $(M+H^+)$; (column: X Select C-18, 50×3.0 mm, 3.5 μm); RT 4.23 min; 5 mM $NH_4OAc$: ACN; 0.8 mL/min).

Step 4: Synthesis of methyl 6-((4-methoxybenzyl)thio) picolinate (8)

To a stirred solution of methyl 6-bromopicolinate 7 (8 g, 37.2 mmol) in 1,4-dioxane (110 mL) under inert atmosphere were added (4-methoxyphenyl)methanethiol (5.7 g, 37.0 mmol), xantphos (1.1 g, 1.9 mmol), diisopropyl ethyl amine (13.6 mL, 74.0 mmol), $Pd_2(dba)_3$ (847 mg, 0.9 mmol) at RT, degassed under argon for 15 min; heated to reflux and stirred for 1 h. After completion of the reaction (TLC), the reaction mixture was diluted with water (500 mL) and extracted with EtOAc (3×500 mL). The combined organic extracts were dried over $Na_2SO_4$, filtered and concentrated under reduced pressure to obtain the crude. The crude was purified (silica gel column chromatography; 10% EtOAc/hexanes) to afford compound 8 (8 g, 75%) as yellow solid. $^1H$ NMR (400 MHz, $CDCl_3$): δ 7.78 (d, J=7.6 Hz, 1H), 7.57 (t, J=8.0 Hz, 1H), 7.42-7.40 (m, 2H), 7.29-7.25 (m, 1H), 6.82 (d, J=8.4 Hz, 2H), 4.44 (s, 2H), 4.00 (s, 3H), 3.77 (s, 3H); LC-MS: 95.7%; 290.3 $(M^++1)$; (column: X Select C-18, 50×3.0 mm, 3.5 μm); RT 4.10 min. 5 mM $NH_4OAc$: ACN; 0.8 mL/min).

Step 5: Synthesis of methyl 6-mercaptopicolinate (6)

A stirred solution of compound 8 (6 g, 20.7 mmol) in Trifluoro acetic acid (50 mL) under inert atmosphere was heated to reflux and stirred for 16 h. After completion of the reaction (TLC), the volatiles were removed under reduced pressure. The residue was diluted with EtOAc (500 mL), washed with aqueous $NaHCO_3$ solution (3×250 mL). The organic extract were dried over $Na_2SO_4$, filtered and concentrated under reduced pressure to obtain the compound 6 (3.5 g, crude) as pale brown solid. LC-MS: 61.1%; 170 $(M^++1)$; (column: X Select C-18, 50×3.0 mm, 3.5 μm); RT 1.41 min. 5 mM $NH_4OAc$: ACN; 0.8 mL/min).

Step 6: Synthesis of methyl 6-((6-chloro-2-cyclopropyl-1-(1-ethyl-1H-pyrazol-4-yl)-7-fluoro-1H-indol-3-yl)thio)picolinate (9)

To a stirred solution of methyl 6-mercaptopicolinate 6 (3.15 g, crude) in $CH_2Cl_2$ (50 mL) under inert atmosphere was added NCS (2.49 g, 18.63 mmol) at RT and stirred for 1 h. To this, indole 5 (5.6 g, 18.47 mmol) in $CH_2Cl_2$ (50 mL) was added at RT and stirred for 16 h. After completion of the reaction (TLC), the reaction mixture was diluted $CH_2Cl_2$ (100 mL) washed with water (3×100 mL). The organic extract was dried over $Na_2SO_4$, filtered and concentrated under reduced pressure to obtain the crude. The crude was purified (silica gel column chromatography; 10% EtOAc/hexanes) to afford 9 (2.8 g, 32%) as a pale brown solid. $^1H$ NMR (500 MHz, DMSO-$d_6$): δ 7.79 (d, J=7.5 Hz, 1H), 7.66 (d, J=10.5 Hz, 2H), 7.51 (t, J=7.5 Hz, 1H), 7.19 (d, J=8.5 Hz, 1H), 7.10-7.07 (m, 1H), 6.78 (d, J=8.0 Hz, 1H), 4.28 (q, 2H), 4.00 (s, 3H), 1.75-1.69 (m, 1H), 1.58 (t, J=7.0 Hz, 3H), 1.09-1.08 (m, 2H), 0.87-0.84 (m, 2H); LC-MS: 98.4%; m/z 471.4 $(M+H^+)$;(column; X-select CSH C-18, (50×3.0 mm, 3.5 μm); RT 4.25 min. 5.0 mM $NH_4OAc$ (Aq): ACN; 0.8 mL/min); HPLC: 98.1%; (column: Acquity BEH C-18 (50×2.1 mm, 1.7μ); RT 3.02 min. ACN: 0.025% TFA (aq); 0.5 mL/min).

Step 7: Synthesis of 6-(6-chloro-2-cyclopropyl-1-(1-ethyl-1H-pyrazol-4-yl)-7-fluoro-1H-indol-3-yl)thio) picolinic acid sodium salt (Compound D sodium salt)

To a stirred solution of compound 9 (2.81 g, 5.97 mmol) in THF:water (4:1) (40 mL) was added 1M aq. NaOH solution (6.03 mL, 6.03 mmol) and the mixture was heated at 60° C. for 1 h. After completion of the reaction, the solvent was removed to afford compound E (2.83 g, 100%) as a light brown solid. LC-MS: 457 $(M^++1)$ Example 5

3-((6-chloro-7-fluoro-2-methyl-1-(2-oxo-2-(spiro [cyclopropane-1,3'-indolin]-1'-yDethyl)-1H-indol-3-yl)thio)-2-fluorobenzoic acid (Compound E)

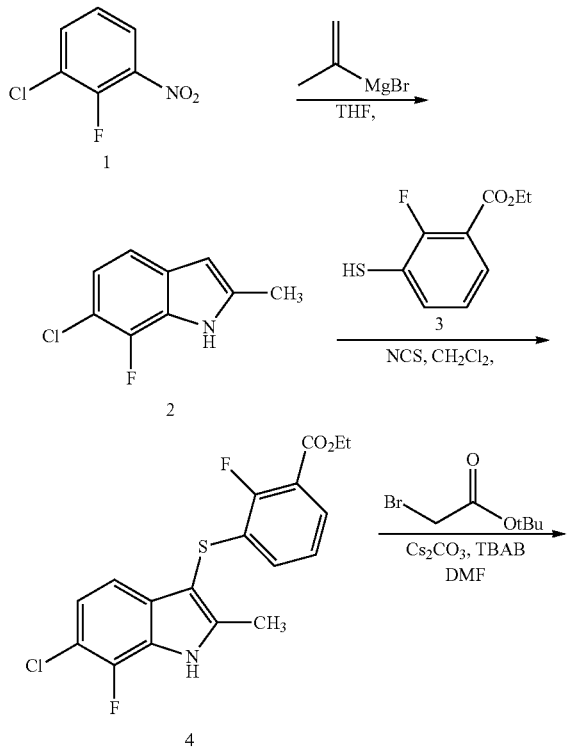

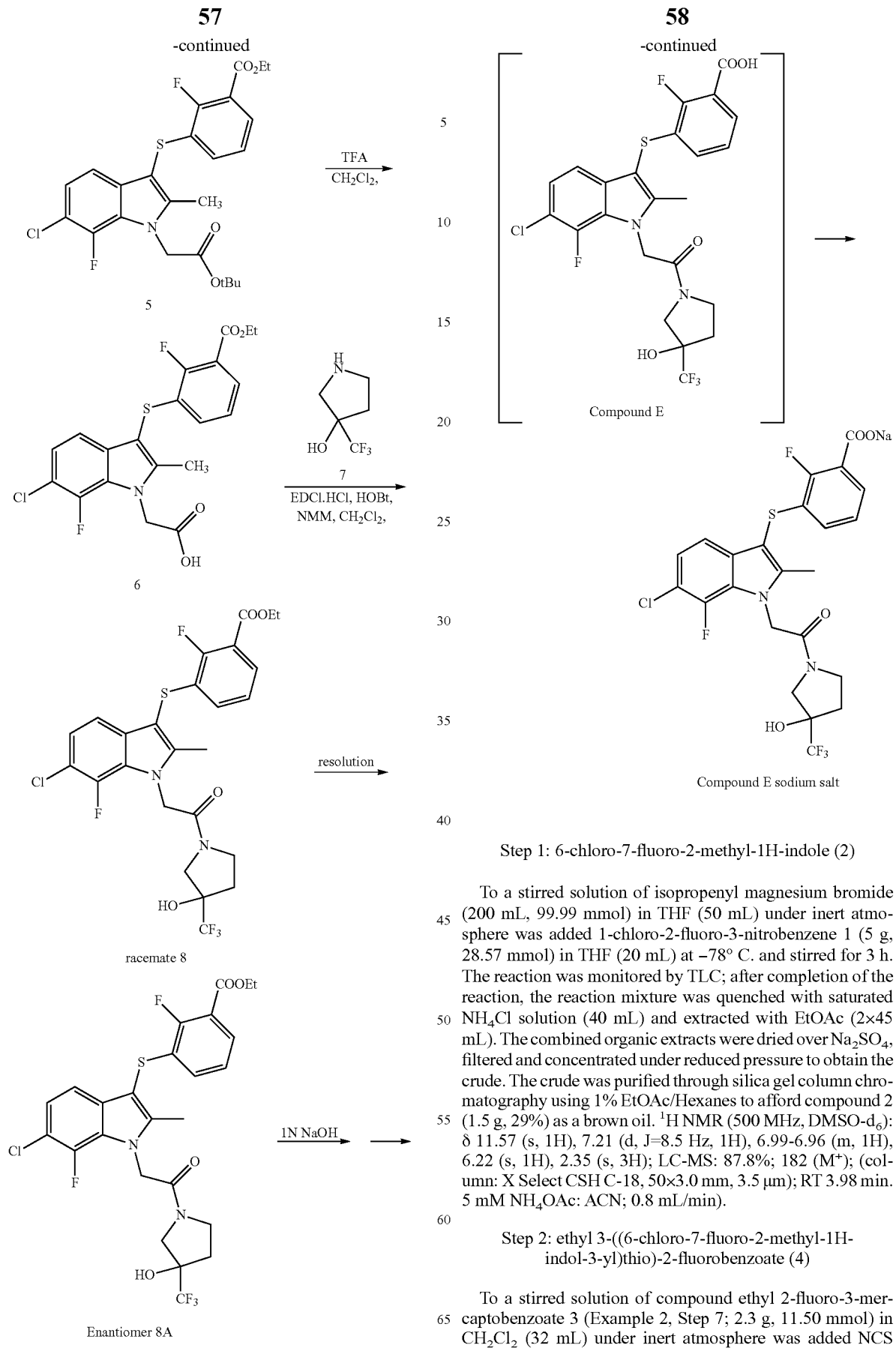

Step 1: 6-chloro-7-fluoro-2-methyl-1H-indole (2)

To a stirred solution of isopropenyl magnesium bromide (200 mL, 99.99 mmol) in THF (50 mL) under inert atmosphere was added 1-chloro-2-fluoro-3-nitrobenzene 1 (5 g, 28.57 mmol) in THF (20 mL) at −78° C. and stirred for 3 h. The reaction was monitored by TLC; after completion of the reaction, the reaction mixture was quenched with saturated $NH_4Cl$ solution (40 mL) and extracted with EtOAc (2×45 mL). The combined organic extracts were dried over $Na_2SO_4$, filtered and concentrated under reduced pressure to obtain the crude. The crude was purified through silica gel column chromatography using 1% EtOAc/Hexanes to afford compound 2 (1.5 g, 29%) as a brown oil. $^1$H NMR (500 MHz, DMSO-$d_6$): δ 11.57 (s, 1H), 7.21 (d, J=8.5 Hz, 1H), 6.99-6.96 (m, 1H), 6.22 (s, 1H), 2.35 (s, 3H); LC-MS: 87.8%; 182 (M$^+$); (column: X Select CSH C-18, 50×3.0 mm, 3.5 μm); RT 3.98 min. 5 mM $NH_4OAc$: ACN; 0.8 mL/min).

Step 2: ethyl 3-((6-chloro-7-fluoro-2-methyl-1H-indol-3-yl)thio)-2-fluorobenzoate (4)

To a stirred solution of compound ethyl 2-fluoro-3-mercaptobenzoate 3 (Example 2, Step 7; 2.3 g, 11.50 mmol) in $CH_2Cl_2$ (32 mL) under inert atmosphere was added NCS (1.69 g, 12.65 mmol) at RT and stirred for 1 h. To this was added 2 (2.10 g, 11.50 mmol) in $CH_2Cl_2$ (10 mL) and stirred for 12 h. The reaction was monitored by TLC; after completion of the reaction, the reaction mixture was diluted with water (20 mL) and extracted with $CH_2Cl_2$ (2×40 mL). The combined organic extracts were dried over $Na_2SO_4$, filtered and concentrated under reduced pressure to obtain the crude. The crude was purified through silica gel column chromatography using 2% EtOAc/Hexanes to afford compound 4 (2.5 g, 57%) as an off-white solid. $^1H$ NMR (500 MHz, DMSO-$d_6$): δ 12.50 (s, 1H), 7.58 (t, J=7.0 Hz, 1H), 7.14 (s, 1H), 7.09 (t, J=8.0 Hz, 2H), 6.79 (t, J=8.0 Hz, 1H), 4.32 (q, 2H), 2.45 (s, 3H), 1.31 (t, J=7.5 Hz, 3H); Mass: 383.2 ($M^++1$).

Step 3: ethyl 3-((1-(2-(tert-butoxy)-2-oxoethyl)-6-chloro-7-fluoro-2-methyl-1H-indol-3-yl)thio)-2-fluorobenzoate (5)

To a stirred solution of compound 4 (140 mg, 0.36 mmol) in DMF (3 mL) under inert atmosphere were added tert-butyl 2-bromoacetate (0.08 mL, 0.54 mmol), $Cs_2CO_3$ (238 mg, 0.73 mmol), $Bu_4NBr$ (5.9 mg, 0.018 mmol) at RT and stirred for 1 h. The reaction was monitored by TLC; after completion of the reaction, the reaction mixture was diluted with water (20 mL) and extracted with EtOAc (2×20 mL). The combined organic extracts were washed with water (15 mL) dried over $Na_2SO_4$, filtered and concentrated under reduced pressure to obtain the crude compound 5 (200 mg) as a pale green semi-solid. $^1H$ NMR (500 MHz, $CDCl_3$): δ 7.61 (t, J=7.0 Hz, 1H), 7.21 (d, J=8.0 Hz, 1H), 7.09 (t, J=8.5 Hz, 1H), 6.90 (t, J=8.5 Hz, 1H), 6.74 (t, J=6.5 Hz, 1H), 4.95 (s, 2H), 4.40 (q, 2H), 2.44 (s, 3H), 1.52 (s, 9H), 1.42 (t, J=7.5 Hz, 3H); LC-MS: 96.7%; 513.6 ($M^+H_2O$); (column: X Select CSH C-18, 50×3.0 mm, 3.5 μm); RT 4.72 min. 5 mM $NH_4OAc$: ACN; 0.8 mL/min).

Step 4: 2-(6-chloro-3-((3-(ethoxycarbonyl)-2-fluorophenyl)thio)-7-fluoro-2-methyl-1H-indol-1-yl) acetic acid (6)

To a stirred solution of compound 5 (200 mg, 0.40 mmol) in $CH_2Cl_2$ (10 mL) under inert atmosphere was added TFA (0.8 mL) at 0° C.; warmed to RT and stirred for 12 h. The reaction was monitored by TLC; after completion of the reaction, the volatiles were removed under reduced pressure. The residue was diluted with water (20 mL) and extracted with $CH_2Cl_2$ (2×30 mL). The combined organic extracts were washed with water (15 mL), dried over $Na_2SO_4$, filtered and concentrated under reduced pressure to obtain the crude. The crude was triturated with n-pentane (2×5 mL) to afford compound 6 (149 mg, 81%) as an off-white solid. $^1H$ NMR (400 MHz, DMSO-$d_6$): δ 7.59-7.55 (m, 1H), 7.19-7.06 (m, 3H), 6.79-6.75 (m, 1H), 4.93 (s, 2H), 4.32 (q, 2H), 2.40 (s, 3H), 1.31 (t, J=7.2 Hz, 3H); LC-MS: 98.7%; 440.3 ($M^++1$); (column: X Select CSH C-18, 50×3.0 mm, 3.5 μm); RT 2.90 min. 5 mM $NH_4OAc$: ACN; 0.8 mL/min).

Step 5: ethyl 3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate racemic 8

To a stirred suspension of compound 6 (5.69 g, 12.9 mmol) in $CH_2Cl_2$ (65 mL) was added HATU (7.38 g, 19.4 mmol) and DIEA (2.25 mL, 12.9 mmol) at RT and stirred for 5 min. Then compound 7 (2.97 g, 15.5 mmol) and DIEA (7.85 mL, 38.7 mmol) was added and the reaction stirred at RT for 1 h. After the completion of the reaction, the mixture was washed with water. The aqueous layer was back extracted (2×DCM) and all the organic layers were combined. The combined organics was washed with brine, dried over $Na_2SO_4$, filtered, and concentrated under reduced pressure to obtain the crude material. The crude was purified through silica gel column chromatography using 0-50% EtOAc/DCM and then 0-50% EtOAc/Hexanes to afford compound 8 as a racemate (6.6 g, 88%) as a tangerine solid. LC-MS: 577 ($M^++1$)

Step 6: Resolution: ethyl 3-((6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate Enantiomer 8A Racemic compound 8 (11 g) was purified by chiral chromatography using Chiralpak-AD-H column eluting with 90:10 of Phase A (0.1% TFA in n-hexane): Phase B (EtOH: MeOH 50:50). The first eluted compound was collected to give compound 8A (4.3 g). HPLC: 98.6%; (column: Acquity BEH C-18 (50×2.1 mm, 1.7μ); RT 3.10 min. ACN: 0.025% TFA (aq); 0.5 mL/min). LC-MS: 577.5 ($M^++1$)

Step 7: 34(6-chloro-7-fluoro-1-(2-(3-hydroxy-3-(trifluoromethyl)pyrrolidin-1-yl)-2-oxoethyl)-2-methyl-1H-indol-3-yl)thio)-2-fluorobenzoate (Compound E)

To a solution of compound 8A (4.35 g, 7.54 mmol) in THF:water (3:1) (30 mL) was added 1M aq. NaOH solution (7.92 mL, 7.92 mmol) at RT and then heat at 60° C. overnight. The next day additional 1M aq. NaOH solution (0.23 mL, 0.23 mmol) was added to the reaction and heated at 60° C. for 5.5 h. After the completion of the reaction, solvent was removed to afford Compound E sodium salt (4.30 g, 100%) as a beige solid. $^1H$ NMR (300 MHz, DMSO-$d_6$): δ 7.20-7.10 (m, 3H), 6.77 (t, 1H), 6.40-6.35 (m, 1H), 5.31-5.16 (m, 2H), 3.91-3.69 (m, 5H), 2.36 (d, 3H), 2.17-1.97 (m, 2H); LC-MS: 549 ($M^++1$)

Example 6

Human Autotaxin Assay

ATX activity is assayed in concentrated conditioned media from Hep3B human hepatocellular carcinoma cells by measuring the amount of choline released from the substrate, lysophosphatidylcholine (LPC) as it is cleaved to LPA. Conditioned media is collected from confluent Hep3B cells and concentrated 20-fold using Centriprep-30 filter devices (Millipore). To assay for autotaxin inhibition, 10-20 μL of the concentrated conditioned media is incubated with 2.5 μL of a test compound in DMSO and 72.5-82.5 μL lyso-PLD buffer (100 mM Tris pH 9, 500 mM NaCl, 5 mM $MgCl_2$, 5 mM $CaCl_2$, 0.05% Triton X-100 in the presence or absence of 0.2% fatty-acid-free human serum albumin) for 15 min at 37° C. After the 15 min incubation, 5 ul of 2 mM LPC (14:0; Avanti Polar Lipids Cat#855575C) diluted in lyso-PLD buffer is added for a final concentration of 100 uM and the incubation continues for 1.5-3 hours at 37° C. 100 μl of a color mix containing 4.5 mM 4-aminoantipyrine, 2.7 mM N-ethyl-N-(2-hydroxy-3-sulfopropyl)-m-toluidine, 21 units/ml horseradish peroxidase and 3 units/ml choline oxidase in 50 mM Tris, pH 8, 4.5 mM $MgCl_2$ is added and the incubation continued for 15 minutes at room temperature before reading the absorbance at 555 nm.

Illustrative biological activity of representative compounds in the human autotaxin assay described herein is presented in the following table:

| Compound | IC$_{50}$ (µM) |
| --- | --- |
| Compound A | A |
| Compound B | A |
| Compound C | A |
| Compound D | A |
| Compound E | A |

A is ≤0.5 µM; B is >0.5 µM but ≤1 µM; C >1 µM.

Example 7

Effects of Autotaxin Inhibitors on Glucose Tolerance in Mice Fed a High Fat Diet C57B16/J male mice were fed a normal diet until 9-10 weeks of age. Mice were then fed either a normal diet (ND) or high-fat diet (HFD) (20% protein, 35% carbohydrate, 45% fat; Harlan Laboratories) for 8-10 weeks. For determination of blood glucose, mice were administered test compound orally in 0.5% methocel once or twice daily for several days prior to the glucose challenge. Compounds were administered as a sodium salt. On the day of the glucose tolerance test (GTT) mice were fasted for 6-8 hours and a last dose of test compound administered orally 1-3 hours before the intraperitoneal (i.p.) injection of 1 g/kg D-glucose (Sigma). Blood from the tail vein was sampled before the glucose load (baseline glucose) and every 15-30 min over the next 120 min after the glucose challenge to monitor blood glucose concentration. Blood glucose was quantified using a glucose meter (Accu-Chek, Roche Diagnostics or AlphaTRAK, Abbott Animal Health) and plotted vs. time. Total blood glucose area under the curve (AUC) after the i.p. glucose challenge was calculated from the time plot using GraphPad Prism6.

As shown in FIG. 1, Compound A (30 mg/kg) and Compound C (15 mg/kg) twice daily for two days prior to sampling and once on the day of sampling decrease baseline glucose and total blood glucose AUC.

Figure 2:
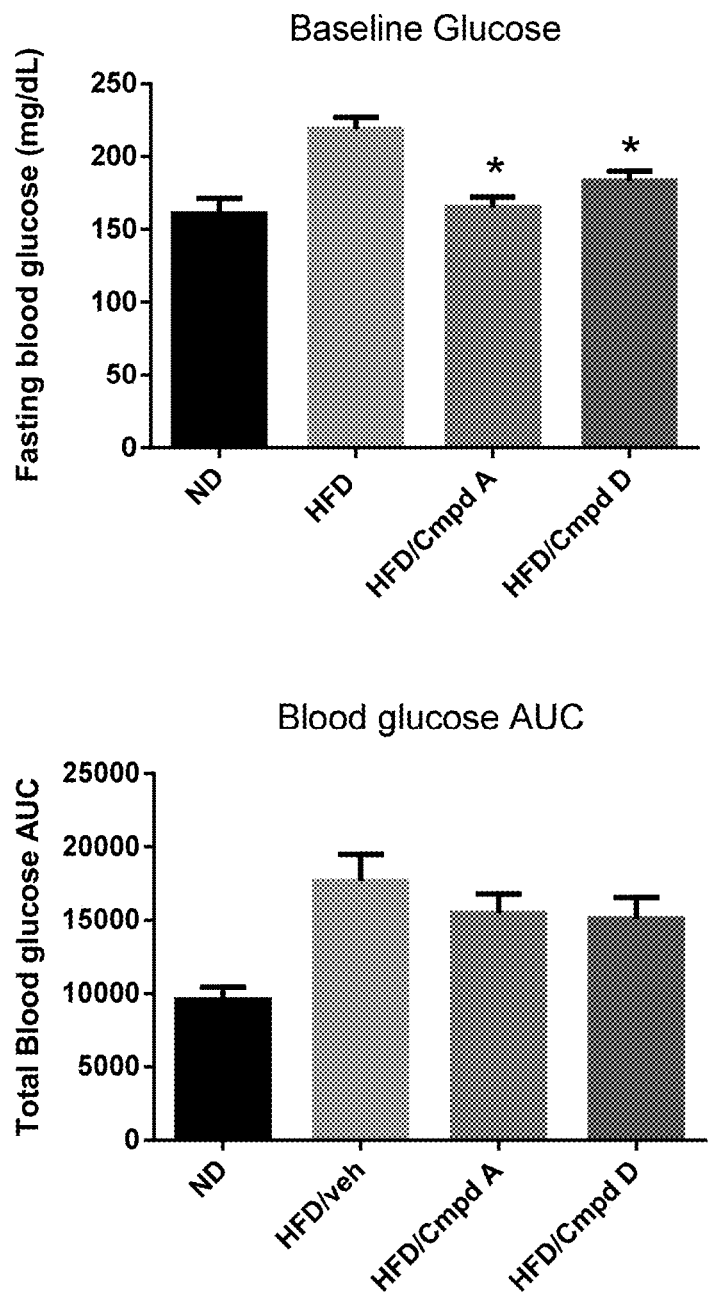
FIG. 2 illustrates the effects of autotaxin inhibitors (Compound A and Compound D) on fasting blood glucose levels in mice fed a high fat diet (HFD). Baseline fasting blood glucose (top graph) from normal mice and high fat diet mice dosed orally with vehicle (veh), Compound A (30 mg/kg) or Compound D (30 mg/kg) twice daily for two days prior to sampling and once on the day of sampling. Total blood glucose AUC (bottom graph) from these same mice after an i.p. challenge with 1 g/kg glucose. * $p<0.02$ using t-test.

As shown in FIG. 2, Compound A (30 mg/kg) or Compound D (30 mg/kg) twice daily for two days prior to sampling and once on the day of sampling decrease baseline glucose and total blood glucose AUC.

Figure 3:
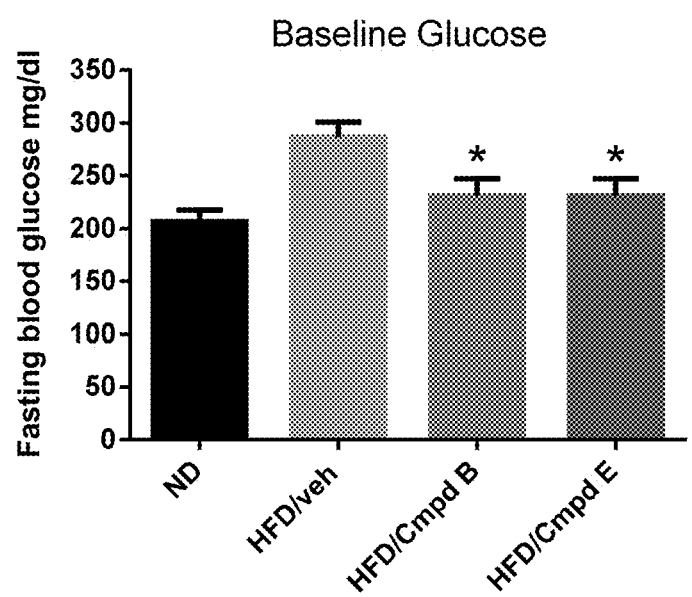
FIG. 3 illustrates the effects of autotaxin inhibitors (Compound B and Compound E) on fasting blood glucose levels in mice fed a high fat diet (HFD). Baseline fasting blood glucose from normal diet mice and high fat diet mice dosed orally with vehicle (veh), Compound B (30 mg/kg) or Compound E (30 mg/kg) once daily for 5 days prior to sampling. * $p<0.02$ using t-test.

As shown in FIG. 3, Compound B (30 mg/kg) or Compound E (30 mg/kg) once daily for 5 days prior to sampling decrease baseline glucose.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for reducing blood glucose levels in an individual with a metabolic disorder in need thereof comprising administering to said individual a selective small molecule autotaxin inhibitor.

2. The method of claim 1, wherein blood glucose levels decrease in the individual by at least 10% following the administering of said autotaxin inhibitor.

3. The method of claim 1, wherein blood lysophosphatidic acid (LPA) levels in said individual decrease by at least 20% following the administering of said autotaxin inhibitor.

4. The method of claim 1, wherein the autotaxin inhibitor is an indole containing small molecule.

5. The method of claim 1, wherein the individual has elevated glucose levels.

6. The method of claim 1, wherein the blood glucose levels in the individual are greater than 100 mg/dl prior to administration of the autotaxin inhibitor.

7. The method of claim 1, wherein the individual has metabolic syndrome.

8. The method of claim 1, wherein the individual has at least one medical condition selected from the group consisting of: abdominal obesity, elevated blood pressure, elevated fasting plasma glucose, high serum triglycerides, and low high-density cholesterol levels (HDL).

9. The method of claim 1, wherein the individual has insulin resistance.

10. The method of claim 1, wherein the individual has type 2 diabetes.

11. The method of claim 1, wherein the individual has A1C levels that are at least 6.0% or greater.

12. The method of claim 1, wherein the individual has been diagnosed with non-alcoholic fatty liver disease (NAFLD) or nonalcoholic steatohepatitis.

13. The method of claim 1, wherein the individual has an impaired glucose tolerance.

14. The method of claim 1, wherein the individual is prediabetic.

15. The method of claim 14, wherein the individual has a body mass index of at least 25 kg/m$^2$ and at least one or more of the diabetes risk factors selected from the group consisting of: physical inactivity, a first-degree relative with diabetes, a high-risk race or ethnicity, a woman that delivered a baby weighing more than 9 pounds, a woman previously diagnosed with gestational diabetes, hypertensive, HDL cholesterol levels lower than at least 0.9 mmol/L (35 mg/dL), triglyceride levels at least 2.82 mmol/L (250 mg/dL) or greater, woman with polycystic ovarian syndrome, severe obesity, acanthosis nigrican, and cardiovascular disease.

16. The method of claim 1, wherein the individual is obese.

17. The method of claim 1, further comprising administering an additional therapeutic agent to the individual.

18. The method of claim 17, wherein the additional therapeutic agent is selected from the group consisting of: peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a human amylin analog, a biguanide, a glucophage, an alpha-glucosidase inhibitor, a meglitinide, a thiazolidinedione, and sulfonylurea, or any combination thereof.

19. The method of claim 17, wherein the additional therapeutic agent is selected from the group consisting of: an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, and a fibrate, or any combination thereof.

* * * * *